Figure 1:
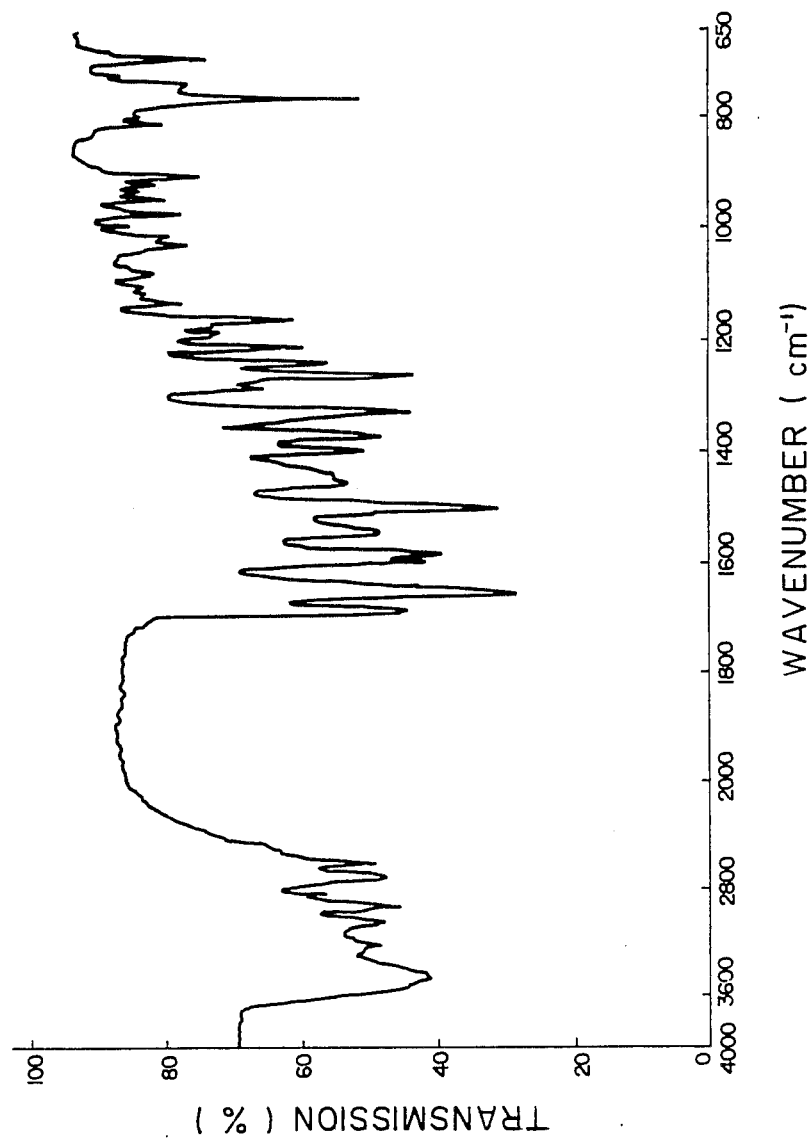

United States Patent [19]

Fukami et al.

[11] Patent Number: 4,613,598
[45] Date of Patent: Sep. 23, 1986

[54] PIPERAZINE DERIVATIVES AND THEIR ACID ADDITION SALTS

[75] Inventors: Harukazu Fukami, Kyoto; Shinya Inoue, Yokohama; Issei Nitta, Machida; Kenichiro Nakao, Tokyo; Ryoji Kikumoto, Machida, all of Japan

[73] Assignee: Mitsubishi Chemical Industries Limited, Tokyo, Japan

[21] Appl. No.: 708,641

[22] Filed: Mar. 6, 1985

[30] Foreign Application Priority Data

Mar. 13, 1984 [JP] Japan ................... 59-47964
Mar. 13, 1984 [JP] Japan ................... 59-47965
Mar. 13, 1984 [JP] Japan ................... 59-47966

[51] Int. Cl.[4] .................. A61K 31/55; C07D 417/10
[52] U.S. Cl. ........................ 514/211; 514/225; 514/239; 514/255; 544/58.2; 544/105; 544/360; 544/392; 544/393; 544/394; 540/491
[58] Field of Search ............ 260/239.3 B; 544/58.2, 544/105, 360, 392, 393, 394; 514/211, 225, 239, 255

[56] References Cited

U.S. PATENT DOCUMENTS 3,538,090 11/1970 De Stevens ............ 544/360
4,515,793 5/1985 Werbel et al. ............ 544/394

FOREIGN PATENT DOCUMENTS 872352 7/1961 United Kingdom ............ 546/392

*Primary Examiner*—Robert T. Bond
*Attorney, Agent, or Firm*—Oblon, Fisher, Spivak, McClelland & Maier

[57] ABSTRACT

A piperazine derivative according to the present invention has the following general formula [I]:

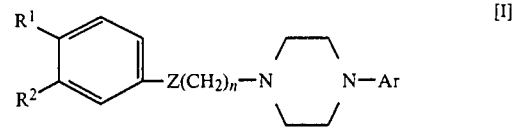

wherein
$R^1$ is —OH, —OR$^3$, —SR$^3$, —SOR$^3$ or —SO$_2$R$^3$ wherein $R^3$ is alkyl group having 1 to 3 carbon atoms;
$R^2$ is —SO$_2$NH$_2$, —SO$_2$NHR$^4$, —SO$_2$NR$^4$R$^5$, —COOH, —COOR$^4$, —CONH$_2$, —CONHR$^4$, —CONR$^4$R$^5$, —NHCONH$_2$, —NHCSNH$_2$, —NHCONHR$^4$, —NHCOR$^4$ or —NHSO$_2$R$^4$ wherein $R^4$ and $R^5$ are independently alkyl group having 1 to 3 carbon atoms; or
$R^1$ and $R^2$ together with carbon atoms to which they are attached form

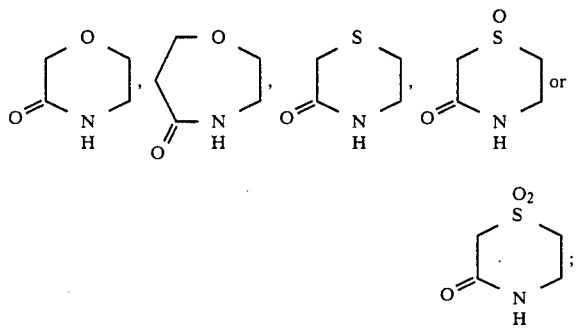

Z is —CO— or —CH(OH)—;
Ar is pyridyl or substituted or unsubstituted phenyl; and
n is an integer of 3 to 5.

An acid addition salt of the piperazine derivative having the above formula [I] is included in the present invention. The piperazine derivative as well as its acid addition salt according to the present invention have the ability to reduce the blood pressure.

7 Claims, 9 Drawing Figures

PIPERAZINE DERIVATIVES AND THEIR ACID ADDITION SALTS

The present invention relates to piperazine derivatives and acid addition salts thereof having an ability to reduce the blood pressure.

In particular, the present invention relates to compounds of the general formula [I]:

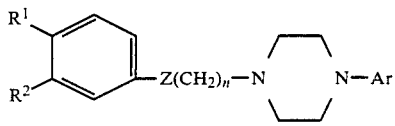

wherein $R^1$ is —OH, —OR$^3$, —SR$^3$, —SOR$^3$ or —SO$_2$R$^3$ wherein $R^3$ is alkyl group having 1 to 3 carbon atoms;
$R^2$ is —SO$_2$NH$_2$, —SO$_2$NHR$^4$, —SO$_2$NR$^4$R$^5$, —COOH, —COOR$^4$, —CONH$_2$, —CONHR$^4$, —CONR$^4$R$^5$, —NHCONH$_2$, —NHCSNH$_2$, —NHCONHR$^4$, —NHCOR$^4$ or —NHSO$_2$R$^4$ wherein $R^4$ and $R^5$ are independently alkyl group having 1 to 3 carbon atoms; or
$R^1$ and $R^2$ together with carbon atoms to which they are attached form

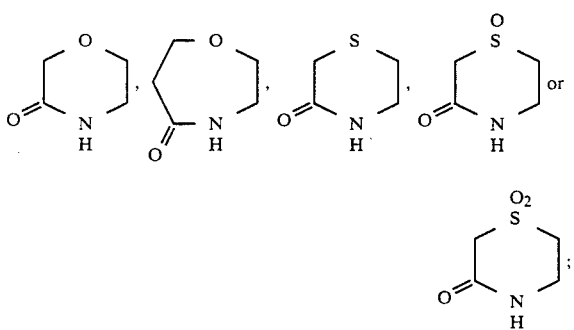

Z is —CO— or —CH(OH)—;
Ar is pyridyl or substituted or unsubstituted phenyl; and
n is an integer of 3 to 5, and their acid addition salts.

A substituent which may be carried by phenyl as Ar is halogen, alkyl having 1 to 3 carbon atoms or alkoxy having 1 to 3 carbon atoms, preferably alkoxy.

Typical and non-limitative examples of the compounds of the general formula [I] according to the present invention (hereinafter referred to as "the present compound") are as follows.

5-[4-(4-phenyl-1-piperazinyl)butyryl]-2-methoxybenzenesulfonamide,
5-[5-(4-phenyl-1-piperazinyl)valeryl]-2-methoxybenzenesulfonamide,
5-[6-(4-phenyl-1-piperazinyl)caproyl]-2-methoxybenzenesulfonamide,
5-[4-(4-phenyl-1-piperazinyl)-1-hydroxybutyl]-2-methoxybenzenesulfonamide,
5-[5-(4-phenyl-1-piperazinyl)-1-hydroxypentyl]-2-methoxybenzenesulfonamide,
5-[6-(4-phenyl-1-piperazinyl)-1-hydroxyhexyl]-2-methoxybenzenesulfonamide,
5-[4-(4-phenyl-1-piperazinyl)butyryl]-2-methoxy-N-methylbenzenesulfonamide,
5-[5-(4-phenyl-1-piperazinyl)valeryl]-2-methoxy-N-methylbenzenesulfonamide,
5-[6-(4-phenyl-1-piperazinyl)caproyl]-2-methoxy-N-methylbenzenesulfonamide,
5-[4-(4-phenyl-1-piperazinyl)-1-hydroxybutyl]-2-methoxy-N-methylbenzenesulfonamide,
5-[5-(4-phenyl-1-piperazinyl)-1-hydroxypentyl]-2-N-methylbenzenesulfonamide,
5-[6-(4-phenyl-1-piperazinyl)-1-hydroxyhexyl]-2-methoxy-N-methylbenzenesulfonamide,
5-[4-(4-phenyl-1-piperazinyl)butyryl]-2-methoxy-N,N-dimethylbenzenesulfonamide,
5-[5-(4-phenyl-1-piperazinyl)valeryl]-2-methoxy-N,N-dimethylbenzenesulfonamide,
5-[6-(4-phenyl-1-piperazinyl)caproyl]-2-methoxy-N,N-dimethylbenzenesulfonamide,
5-[4-(4-phenyl-1-piperazinyl)-1-hydroxybutyl]-2-methoxy-N,N-dimethylbenzenesulfonamide,
5-[5-(4-phenyl-1-piperazinyl)-1-hydroxypentyl]-2-methoxy-N,N-dimethylbenzenesulfonamide,
5-[6-(4-phenyl-1-piperazinyl)-1-hydroxyhexyl]-2-methoxy-N,N-dimethylbenzenesulfonamide,
5-[4-(4-phenyl-1-piperazinyl)butyryl]-2-methylthiobenzenesulfonamide,
5-[5-(4-phenyl-1-piperazinyl)valeryl]-2-methylthiobenzenesulfonamide,
5-[6-(4-phenyl-1-piperazinyl)caproyl]-2-methylthiobenzenesulfonamide,
5-[4-(4-phenyl-1-piperazinyl)-1-hydroxybutyl]-2-methylthiobenzenesulfonamide,
5-[5-(4-phenyl-1-piperazinyl)-1-hydroxypentyl]-2-methylthiobenzenesulfonamide,
5-[6-(4-phenyl-1-piperazinyl)-1-hydroxyhexyl]-2-methylthiobenzenesulfonamide,
5-[4-(4-phenyl-1-piperazinyl)butyryl]-2-methylthio-N-methylbenzenesulfonamide,
5-[5-(4-phenyl-1-piperazinyl)valeryl]-2-methylthio-N-methylbenzenesulfonamide,
5-[6-(4-phenyl-1-piperazinyl)caproyl]-2-methylthio-N-methylbenzenesulfonamide,
5-[4-(4-phenyl-1-piperazinyl)-1-hydroxybutyl]-2-methylthio-N-methylbenzenesulfonamide,
5-[5-(4-phenyl-1-piperazinyl)-1-hydroxypentyl]-2-methylthio-N-methylbenzenesulfonamide,
5-[6-(4-phenyl-1-piperazinyl)-1-hydroxyhexyl]-2-methylthio-N-methylbenzenesulfonamide,
5-[4-(4-phenyl-1-piperazinyl)butyryl]-2-methylthio-N,N-dimethylbenzenesulfonamide,
5-[5-(4-phenyl-1-piperazinyl)valeryl]-2-methylthio-N,N-dimethylbenzenesulfonamide,
5-[6-(4-phenyl-1-piperazinyl)caproyl]-2-methylthio-N,N-dimethylbenzenesulfonamide,
5-[4-(4-phenyl-1-piperazinyl)-1-hydroxybutyl]-2-methylthio-N,N-dimethylbenzenesulfonamide,
5-[5-(4-phenyl-1-piperazinyl)-1-hydroxypentyl]-2-methylthio-N,N-dimethylbenzenesulfonamide,
5-[6-(4-phenyl-1-piperazinyl)-1-hydroxyhexyl]-2-methylthio-N,N-dimethylbenzenesulfonamide,
5-[4-(4-phenyl-1-piperazinyl)butyryl]-2-methylsulfinylbenzenesulfonamide,
5-[5-(4-phenyl-1-piperazinyl)valeryl]-2-methylsulfinylbenzenesulfonamide,
5-[6-(4-phenyl-1-piperazinyl)caproyl]-2-methylsulfinylbenzenesulfonamide,
5-[4-(4-phenyl-1-piperazinyl)-1-hydroxybutyl]-2-methylsulfinylbenzenesulfonamide,
5-[5-(4-phenyl-1-piperazinyl)-1-hydroxypentyl]-2-methylsulfinylbenzenesulfonamide, 5-[6-(4-phenyl-1-piperazinyl)-1-hydroxyhexyl]-2-methylsulfinylbenzenesulfonamide,
5-[4-(4-phenyl-1-piperazinyl)butyryl]-2-methylsulfinyl-N-methylbenzenesulfonamide,
5-[5-(4-phenyl-1-piperazinyl)valeryl]-2-methylsulfinyl-N-methylbenzenesulfonamide,
5-[6-(4-phenyl-1-piperazinyl)caproyl]-2-methylsulfinyl-N-methylbenzenesulfonamide,
5-[4-(4-phenyl-1-piperazinyl)-1-hydroxybutyl]-2-methylsulfinyl-N-methylbenzenesulfonamide,
5-[5-(4-phenyl-1-piperazinyl)-1-hydroxypentyl]-2-methylsulfinyl-N-methylbenzenesulfonamide,
5-[6-(4-phenyl-1-piperazinyl)-1-hydroxyhexyl]-2-methylsulfinyl-N-methylbenzenesulfonamide,
5-[4-(4-phenyl-1-piperazinyl)butyryl]-2-methylsulfinyl-N,N-dimethylbenzenesulfonamide,
5-[5-(4-phenyl-1-piperazinyl)valeryl]-2-methylsulfinyl-N,N-dimethylbenzenesulfonamide,
5-[6-(4-phenyl-1-piperazinyl)caproyl]-2-methylsulfinyl-N,N-dimethylbenzenesulfonamide,
5-[4-(4-phenyl-1-piperazinyl)-1-hydroxybutyl]-2-methylsulfinyl-N,N-dimethylbenzenesulfonamide,
5-[5-(4-phenyl-1-piperazinyl)-1-hydroxypentyl]-2-methylsulfinyl-N,N-dimethylbenzenesulfonamide,
5-[6-(4-phenyl-1-piperazinyl)-1-hydroxyhexyl]-2-methylsulfinyl-N,N-dimethylbenzenesulfonamide,
5-[4-(4-phenyl-1-piperazinyl)butyryl]-2-methylsulfonylbenzenesulfonamide,
5-[5-(4-phenyl-1-piperazinyl)valeryl]-2-methylsulfonylbenzenesulfonamide,
5-[6-(4-phenyl-1-piperazinyl)caproyl]-2-methylsulfonylbenzenesulfonamide,
5-[4-(4-phenyl-1-piperazinyl)-1-hydroxybutyl]-2-methylsulfonylbenzenesulfonamide,
5-[5-(4-phenyl-1-piperazinyl)-1-hydroxypentyl]-2-methylsulfonylbenzenesulfonamide,
5-[6-(4-phenyl-1-piperazinyl)-1-hydroxyhexyl]-2-methylsulfonylbenzenesulfonamide,
5-[4-(4-phenyl-1-piperazinyl)butyryl]-2-methylsulfonyl-N-methylbenzenesulfonamide,
5-[5-(4-phenyl-1-piperazinyl)valeryl]-2-methylsulfonyl-N-methylbenzenesulfonamide,
5-[6-(4-phenyl-1-piperazinyl)caproyl]-2-methylsulfonyl-N-methylbenzenesulfonamide,
5-[4-(4-phenyl-1-piperazinyl)-1-hydroxybutyl]-2-methylsulfonyl-N-methylbenzenesulfonamide,
5-[5-(4-phenyl-1-piperazinyl)-1-hydroxypentyl]-2-methylsulfonyl-N-methylbenzenesulfonamide,
5-[6-(4-phenyl-1-piperazinyl)-1-hydroxyhexyl]-2-methylsulfonyl-N-methylbenzenesulfonamide,
5-[4-(4-phenyl-1-piperazinyl)butyryl]-2-methylsulfonyl-N,N-dimethylbenzenesulfonamide,
5-[5-(4-phenyl-1-piperazinyl)valeryl]-2-methylsulfonyl-N,N-dimethylbenzenesulfonamide,
5-[6-(4-phenyl-1-piperazinyl)caproyl]-2-methylsulfonyl-N,N-dimethylbenzenesulfonamide,
5-[4-(4-phenyl-1-piperazinyl)-1-hydroxybutyl]-2-methylsulfonyl-N,N-dimethylbenzenesulfonamide,
5-[5-(4-phenyl-1-piperazinyl)-1-hydroxypentyl]-2-methylsulfonyl-N,N-dimethylbenzenesulfonamide,
5-[6-(4-phenyl-1-piperazinyl)-1-hydroxyhexyl]-2-methylsulfonyl-N,N-dimethylbenzenesulfonamide,
5-[4-(4-phenyl-1-piperazinyl)butyryl]salicylamide,
5-[5-(4-phenyl-1-piperazinyl)valeryl]salicylamide,
5-[6-(4-phenyl-1-piperazinyl)caproyl]salicylamide,
5-[4-(4-phenyl-1-piperazinyl)-1-hydroxybutyl]salicylamide,
5-[5-(4-phenyl-1-piperazinyl)-1-hydroxypentyl]salicylamide,
5-[6-(4-phenyl-1-piperazinyl)-1-hydroxyhexyl]salicylamide,
5-[4-(4-phenyl-1-piperazinyl)butyryl]-N,N-dimethylsalicylamide,
5-[5-(4-phenyl-1-piperazinyl)valeryl]-N,N-dimethylsalicylamide,
5-[6-(4-phenyl-1-piperazinyl)caproyl]-N,N-dimethylsalicylamide,
5-[4-(4-phenyl-1-piperazinyl)-1-hydroxybutyl]-N,N-dimethylsalicylamide,
5-[5-(4-phenyl-1-piperazinyl)-1-hydroxypentyl]-N,N-dimethylsalicylamide,
5-[6-(4-phenyl-1-piperazinyl)-1-hydroxyhexyl]-N,N-dimethylsalicylamide,
5-[4-(4-phenyl-1-piperazinyl)butyryl]-N-methylsalicylamide,
5-[5-(4-phenyl-1-piperazinyl)valeryl]-N-methylsalicylamide,
5-[6-(4-phenyl-1-piperazinyl)coproyl]-N-methylsalicylamide,
5-[4-(4-phenyl-1-piperazinyl)-1-hydroxybutyl]-N-methylsalicylamide,
5-[5-(4-phenyl-1-piperazinyl)-1-hydroxypentyl]-N-methylsalicylamide,
5-[6-(4-phenyl-1-piperazinyl)-1-hydroxyhexyl]-N-methylsalicylamide,
Methyl 5-[4-(4-phenyl-1-piperazinyl)butyryl]salicylate,
Methyl 5-[5-(4-phenyl-1-piperazinyl)valeryl]salicylate,
Methyl 5-[6-(4-phenyl-1-piperazinyl)caproyl]salicylate,
Methyl 5-[4-(4-phenyl-1-piperazinyl)-1-hydroxybutyl]salicylate,
Methyl 5-[5-(4-phenyl-1-piperazinyl)-1-hydroxypentyl]salicylate,
Methyl 5-[6-(4-phenyl-1-piperazinyl)-1-hydroxyhexyl]salicylate,
Ethyl 5-[4-(4-phenyl-1-piperazinyl)butyryl]salicylate,
Ethyl 5-[5-(4-phenyl-1-piperazinyl)valeryl]salicylate,
Ethyl 5-[6-(4-phenyl-1-piperazinyl)caproyl]salicylate,
Ethyl 5-[4-(4-phenyl-1-piperazinyl)-1-hydroxybutyl]salicylate,
Ethyl 5-[5-(4-phenyl-1-piperazinyl)-1-hydroxypentyl]salicylate,
Ethyl 5-[6-(4-phenyl-1-piperazinyl)-1-hydroxyhexyl]salicylate,
5-[4-(4-phenyl-1-piperazinyl)butyryl]salicylic acid,
5-[5-(4-phenyl-1-piperazinyl)valeryl]salicylic acid,
5-[6-(4-phenyl-1-piperazinyl)caproyl]salicylic acid,
5-[4-(4-phenyl-1-piperazinyl)-1-hydroxybutyl]salicylic acid,
5-[5-(4-phenyl-1-piperazinyl)-1-hydroxypentyl]salicylic acid,
5-[6-(4-phenyl-1-piperazinyl)-1-hydroxyhexyl]salicylic acid,
5-[4-(4-phenyl-1-piperazinyl)butyryl]-2-methoxy-N-carbamoylaniline,
5-[5-(4-phenyl-1-piperazinyl)valeryl]-2-methoxy-N-carbamoylaniline,
5-[6-(4-phenyl-1-piperazinyl)caproyl]-2-methoxy-N-carbamoylaniline,
5-[4-(4-phenyl-1-piperazinyl)-1-hydroxybutyl]-2-methoxy-N-carbamoylaniline,
5-[5-(4-phenyl-1-piperazinyl)-1-hydroxypentyl]-2-methoxy-N-carbamoylaniline,
5-[6-(4-phenyl-1-piperazinyl)-1-hydroxyhexyl]-2-methoxy-N-carbamoylaniline, 5-[4-(4-phenyl-1-piperazinyl)butyryl]-2-methoxy-N-thiocarbamoylaniline,
5-[5-(4-phenyl-1-piperazinyl)valeryl]-2-methoxy-N-thiocarbamoylaniline,
5-[6-(4-phenyl-1-piperazinyl)caproyl]-2-methoxy-N-thiocarbamoylaniline,
5-[4-(4-phenyl-1-piperazinyl)-1-hydroxybutyl]-2-methoxy-N-thiocarbamoylaniline,
5-[5-(4-phenyl-1-piperazinyl)-1-hydroxypentyl]-2-methoxy-N-thiocarbamoylamiline,
5-[6-(4-phenyl-1-piperazinyl)-1-hydroxyhexyl]-2-methoxy-N-thiocarbamoylaniline,
5-[4-(4-phenyl-1-piperazinyl)butyryl]-2-methoxyacetanilide,
5-[5-(4-phenyl-1-piperazinyl)valeryl]-2-methoxyacetanilide,
5-[6-(4-phenyl-1-piperazinyl)caproyl]-2-methoxyacetanilide,
5-[4-(4-phenyl-1-piperazinyl)-1-hydroxybutyl]-2-methoxyacetanilide,
5-[5-(4-phenyl-1-piperazinyl)-1-hydroxypentyl]-2-methoxyacetanilide,
5-[6-(4-phenyl-1-piperazinyl)-1-hydroxyhexyl]-2-methoxyacetanilide,
5-[4-(4-phenyl-1-piperazinyl)butyryl]-2-methoxy-N-methanesulfonylaniline,
5-[5-(4-phenyl-1-piperazinyl)valeryl]-2-methoxy-N-methanesulfonylaniline,
5-[6-(4-phenyl-1-piperazinyl)caproyl]-2-methoxy-N-methanesulfonylaniline,
5-[4-(4-phenyl-1-piperazinyl)-1-hydroxybutyl]-2-methoxy-N-methanesulfonylanilane,
5-[5-(4-phenyl-1-piperazinyl)-1-hydroxypentyl]2-methoxy-N-methanesulfonylaniline,
5-[6-(4-phenyl-1-piperazinyl)-1-hydroxyhexyl]-2-methoxy-N-methanesulfonylaniline,
5-[4-(4-phenyl-1-piperazinyl)butyryl]-2-hydroxy-N-carbamoylaniline,
5-[5-(4-phenyl-1-piperazinyl)valeryl]-2-hydroxy-N-carbamoylaniline,
5-[6-(4-phenyl-1-piperazinyl)caproyl]-2-hydroxy-N-carbamoylaniline,
5-[4-(4-phenyl-1-piperazinyl)-1-hydroxybutyl]-2-hydroxy-N-carbamoylaniline,
5-[5-(4-phenyl-1-piperazinyl)-1-hydroxypentyl]-2-hydroxy-N-carbamoylaniline,
5-[6-(4-phenyl-1-piperazinyl)-1-hydroxyhexyl]-2-hydroxy-N-carbamoylaniline,
5-[4-(4-phenyl-1-piperazinyl)butyryl]-2-hydroxy-N-thiocarbamoylaniline,
5-[5-(4-phenyl-1-piperazinyl)valeryl]-2-hydroxy-N-thiocarbamoylaniline,
5-[6-(4-phenyl-1-piperazinyl)caproyl]-2-hydroxy-N-thiocarbamoylaniline,
5-[4-[4-phenyl-1-piperaz-nyl)-1-hydroxybutyl]-2-hydroxy-N-thiocarbamoylaniline,
5-[5-(4-phenyl-1-piperazinyl)-1-hydroxypentyl]-2-hydroxy-N-thiocarbamoylaniline,
5-[6-(4-phenyl-1-piperazinyl)-1-hydroxyhexyl]-2-hydroxy-N-thiocarbamoylaniline,
5-[4-(4-phenyl-1-piperazinyl)butyryl]-2-hydroxyacetanilide,
5-[5-(4-phehyl-1-piperazinyl)valeryl]-2-hydroxyacetanilide,
5-[6-(4-phenyl-1-piperazinyl)caproyl]-2-hydroxyacetanilide,
5-[4-(4-phenyl-1-piperazinyl)-1-hydroxybutyl]-2-hydroxyacetanilide,
5-[5-(4-phenyl-1-piperazinyl)-1-hydroxypentyl]-2-hydroxyacetanilide,
5-[6-(4-phenyl-1-piperazinyl)-1-hydroxyhexyl]-2-hydroxyacetanilide,
5-[4-(4-phenyl-1-piperazinyl)butyryl]-2-hydroxy-N-methanesulfonylaniline,
5-[5-(4-phenyl-1-piperazinyl)valeryl]-2-hydroxy-N-methanesulfonylaniline,
5-[6-(4-phenyl-1-piperazinyl)caproyl]-2-hydroxy-N-methanesulfonylaniline,
5-[4-(4-phenyl-1-piperazinyl)-1-hydroxybutyl]-2-hydroxy-N-methanesulfonylaniline,
5-[5-(4-phenyl-1-piperazinyl)-1-hydroxypentyl]-2-hydroxy-N-methanesulfonylaniline,
5-[6-(4-phenyl-1-piperazinyl)-1-hydroxyhexyl]-2-hydroxy-N-methanesulfonylaniline,
5-[4-(4-phenyl-1-piperazinyl)butyryl]-2-methylthio-N-carbamoylaniline,
5-[5-(4-phenyl-1-piperazinyl)valeryl]-2-methylthio-N-carbamoylaniline,
5-[6-(4-phenyl-1-piperazinyl)caproyl]-2-methylthio-N-carbamoylaniline,
5-[4-(4-phenyl-1-piperazinyl)-1-hydroxybutyl]-2-methylthio-N-carbamoylaniline,
5-[5-(4-phenyl-1-piperazinyl)-1-hydroxypentyl]-2-methylthio-N-carbamoylaniline,
5-[6-(4-phenyl-1-piperazinyl)-1-hydroxyhexyl]-2-methylthio-N-carbamoylaniline,
5-[4-(4-phenyl-1-piperazinyl)butyryl]-2-methylthio-N-thiocarbamoylaniline,
5-[5-(4-phenyl-1-piperazinyl)valeryl]-2-methylthio-N-thiocarbamoylaniline,
5-[6-(4-phenyl-1-piperazinyl)caproyl]-2-methylthio-N-thiocarbamoylaniline,
5-[4-(4-phenyl-1-piperazinyl)-1-hydroxybutyl]-2-methylthio-N-thiocarbamoylaniline,
5-[5-(4-phenyl-1-piperazinyl)-1-hydroxypentyl]-2-methylthio-N-thiocarbamoylaniline,
5-[6-(4-phenyl-1-piperazinyl)-1-hydroxyhexyl]-2-methylthio-N-thiocarbamoylaniline,
5-[4-(4-phenyl-1-piperazinyl)butyryl]-2-methylthioacetanilide,
5-[5-(4-phenyl-1-piperazinyl)valeryl]-2-methylthioacetanilide,
5-[6-(4-phenyl-1-piperazinyl)caproyl]-2-methylthioacetanilide,
5-[4-(4-phenyl-1-piperazinyl)-1-hydroxybutyl]-2-methylthioacetanilide,
5-[5-(4-phenyl-1-piperazinyl)-1-hydroxypentyl]-2-methylthioacetanilide,
5-[6-(4-phenyl-1-piperazinyl)-1-hydroxyhexyl]-2-methylthioacetanilide,
5-[4-(4-phenyl-1-piperazinyl)butyryl]-2-methylthio-N-methanesulfonylaniline,
5-[5-(4-phenyl-1-piperazinyl)valeryl]-2-methylthio-N-methanesulfonylaniline,
5-[6-(4-phenyl-1-piperazinyl)caproyl]-2-methylthio-N-methanesulfonylaniline,
5-[4-(4-phenyl-1-piperazinyl)-1-hydroxybutyl]-2-methylthio-N-methanesulfonylaniline,
5-[5-(4-phenyl-1-piperazinyl)-1-hydroxypentyl]-2-methylthio-N-methanesulfonylaniline,
5-[6-(4-phenyl-1-piperazinyl)-1-hydroxyhexyl]-2-methylthio-N-methanesulfonylaniline,
5-[4-(4-phenyl-1-piperazinyl)butyryl]-2-methylsulfinyl-N-carbamoylaniline,
5-[5-(4-phenyl-1-piperazinyl)valeryl]-2-methylsulfinyl-N-carbamoylaniline, 5-[6-(4-phenyl-1-piperazinyl)caproyl]-2-methylsulfinyl-N-carbamoylaniline,
5-[4-(4-phenyl-1-piperazinyl)-1-hydroxybutyl]-2-methylsulfinyl-N-carbamoylaniline,
5-[5-(4-phenyl-1-piperazinyl)-1-hydroxypentyl]-2-methylsulfinyl-N-carbamoylaniline,
5-[6-(4-phenyl-1-piperazinyl)-1-hydroxyhexyl]-2-methylsulfinyl-N-carbamoylaniline,
5-[4-(4-phenyl-1-piperazinyl)butyryl[-2-methylsulfinyl-N-thiocarbamoylaniline,
5-[5-(4-phenyl-1-piperazinyl)valeryl]-2-methylsulfinyl-N-thiocarbamoylaniline,
5-[6-(4-phenyl-1-piperazinyl)caproyl]-2-methylsulfinyl-N-thiocarbamoylaniline,
5-[4-(4-phenyl-1-piperazinyl)-1-hydroxybutyl]-2-methylsulfinyl-N-thiocarbamoylaniline,
5-[5-(4-phenyl-1-piperazinyl)-1-hydroxypentyl]-2-methylsulfinyl-N-thiocarbamoylaniline,
5-[6-(4-phenyl-1-piperazinyl)-1-hydroxyhexyl]-2-methylsulfinyl-N-thiocarbamoylaniline,
5-[4-(4-phenyl-1-piperazinyl)butyryl]-2-methylsulfinylacetanilide,
5-[5-(4-phenyl-1-piperazinyl)valeryl]-2-methylsulfinylacetanilide,
5-[6-(4-phenyl-1-piperazinyl)caproyl]-2-methylsulfinylacetanilide,
5-[4-(4-phenyl-1-piperazinyl)-1-hydroxybutyl]-2-methylsulfinylacetanilide,
5-[5-(4-phenyl-1-piperazinyl)-1-hydroxypentyl]-2-methylsulfinylacetanilide,
5-[6-(4-phenyl-1-piperazinyl)-1-hydroxyhexyl]-2-methylsulfinylacetanilide,
5-[4-(4-phenyl-1-piperazinyl)butyryl]-2-methylsulfinyl-N-methanesulfonylaniline,
5-[5-(4-phenyl-1-piperazinyl)valeryl]-2-methylsulfinyl-N-methanesulfonylaniline,
5-[6-(4-phenyl-1-piperazinyl)caproyl]-2-methylsulfinyl-N-methanesulfonylaniline,
5-[4-(4-phenyl-1-piperazinyl)-1-hydroxybutyl]-2-methylsulfinyl-N-methanesulfonylaniline,
5-[5-(4-phenyl-1-piperazinyl)-1-hydroxypentyl]-2-methylsulfinyl-N-methanesulfonylaniline,
5-[6-(4-phenyl-1-piperazinyl)-1-hydroxyhexyl]-2-methylsulfinyl-N-methanesulfonylaniline,
5-[4-(4-phenyl-1-piperazinyl)butyryl]-2-methylsulfonyl-N-carbamoylaniline,
5-[5-(4-phenyl-1-piperazinyl)valeryl]-2-methylsulfonyl-N-carbamoylaniline,
5-[6-(4-phenyl-1-piperazinyl)caproyl]-2-methylsulfonyl-N-carbamoylaniline,
5-[4-(4-phenyl-1-piperazinyl)-1-hydroxybutyl]-2-methylsulfonyl-N-carbamoylaniline,
5-[5-(4-phenyl-1-piperazinyl)-1-hydroxypentyl]-2-methylsulfonyl-N-carbamoylaniline,
5-[6-(4-phenyl-1-piperazinyl)-1-hydroxyhexyl]-2-methylsulfonyl-N-carbamoylaniline,
5-[4-(4-phenyl-1-piperazinyl)butyryl]-2-methylsulfonyl-N-thiocarbamoylaniline,
5-[5-(4-phenyl-1-piperazinyl)valeryl]-2-methylsulfonyl-N-thiocarbamoylaniline,
5-[6-(4-phenyl-1-piperazinyl)caproyl]-2-methylsulfonyl-N-thiocarbamoylaniline,
5-[4-(4-phenyl-1-piperazinyl)-1-hydroxybutyl]-2-methylsulfonyl-N-thiocarbamoylaniline,
5-[5-(4-phenyl-1-piperazinyl)-1-hydroxypentyl]-2-methylsulfonyl-N-thiocarbamoylaniline,
5-[6-(4-phenyl-1-piperazinyl)-1-hydroxyhexyl]-2-methylsulfonyl-N-thiocarbamoylaniline,
5-[4-(4-phenyl-1-piperazinyl)butyryl]-2-methylsulfonylacetanilide,
5-[5-(4-phenyl-1-piperazinyl)valeryl]-2-methylsulfonylacetanilide,
5-[6-(4-phenyl-1-piperazinyl)caproyl]-2-methylsulfonylacetanilide,
5-[4-(4-phenyl-1-piperazinyl)-1-hydroxybutyl]-2-methylsulfonylacetanilide,
5-[5-(4-phenyl-1-piperazinyl)-1-hydroxypentyl]-2-methylsulfonylacetanilide,
5-[6-(4-phenyl-1-piperazinyl)-1-hydroxyhexyl]-2-methylsulfonylacetanilide,
5-[4-(4-phenyl-1-piperazinyl)butyryl]-2-methylsulfonyl-N-methanesulfonylaniline,
5-[5-(4-phenyl-1-piperazinyl)valeryl]-2-methylsulfonyl-N-methanesulfonylaniline,
5-[6-(4-phenyl-1-piperazinyl)caproyl]-2-methylsulfonyl-N-methanesulfonylaniline,
5-[4-(4-phenyl-1-piperazinyl)-1-hydroxybutyl]-2-methylsulfonyl-N-methanesulfonylaniline,
5-[5-(4-phenyl-1-piperazinyl)-1-hydroxypentyl]-2-methylsulfonyl-N-methanesulfonylaniline,
5-[6-(4-phenyl-1-piperazinyl)-1-hydroxyhexyl]-2-methylsulfonyl-N-methanesulfonylaniline,
6-[4-(4-phenyl-1-piperazinyl)butyryl]-2,3-dihydro-4H-1,4-benzoxazine-3-one,
6-[5-(4-phenyl-1-piperazinyl)valeryl]-2,3-dihydro-4H-1,4-benzoxazine-3-one,
6-[6-(4-phenyl-1-piperazinyl)caproyl]-2,3-dihydro-4H-1,4-benzoxazine-3-one,
6-[4-(4-phenyl-1-piperazinyl)-1-hydroxybutyl]-2,3-dihydro-4H-1,4-benzoxazine-3-one,
6-[5-(4-phenyl-1-piperazinyl)-1-hydroxypentyl]-2,3-dihydro-4H-1,4-benzoxazine-3-one,
6-[6-(4-phenyl-1-piperazinyl)-1-hydroxyhexyl]-2,3-dihydro-4H-1,4-benzoxazine-3-one,
7-[4-(4-phenyl-1-piperazinyl)butyryl]-2,3,4,5-tetrahydro-1,5-benzoxazepine-4-one,
7-[5-(4-phenyl-1-piperazinyl)valeryl]-2,3,4,5-tetrahydro-1,5-benzoxazepine-4-one,
7-[6-(4-phenyl-1-piperazinyl)caproyl]-2,3,4,5-tetrahydro-1,5-benzoxazepine-4-one,
7-[4-(4-phenyl-1-piperazinyl)-1-hydroxybutyl]-2,3,4,5-tetrahydro-1,5-benzoxazepine-4-one,
7-[5-(4-phenyl-1-piperazinyl)-1-hydroxypentyl]-2,3,4,5-tetrahydro-1,5-benzoxazepine-4-one,
7-[6-(4-phenyl-1-piperazinyl)-1-hydroxyhexyl]-2,3,4,5-tetrahydro-1,5-benzoxazepine-4-one,
6-[4-(4-phenyl-1-piperazinyl)butyryl]-2,3-dihydro-4H-1,4-benzothiazine-3-one,
6-[5-(4-phenyl-1-piperazinyl)valeryl]-2,3-dihydro-4H-1,4-benzothiazine-3-one,
6-[6-(4-phenyl-1-piperazinyl)caproyl]-2,3-dihydro-4H-1,4-benzothiazine-3-one,
6-[4-(4-phenyl-1-piperazinyl)-1-hydroxybutyl]-2,3-dihydro-4H-1,4-benzothiazine-3-one,
6-[5-(4-phenyl-1-piperazinyl)-1-hydroxypentyl]-2,3-dihydro-4H-1,4-benzothiazine-3-one,
6-[6-(4-phenyl-1-piperazinyl)-1-hydroxyhexyl]-2,3-dihydro-4H-1,4-benzothiazine-3-one,
6-[4-(4-phenyl-1-piperazinyl)butyryl]-2,3-dihydro-,4H-1,4-benzothiazine-3-one 1-oxide,
6-[5-(4-phenyl-1-piperazinyl)valeryl]-2,3-dihydro-4H-1,4-benzothiazine-3-one 1-oxide,
6-[6-(4-phenyl-1-piperazinyl)caproyl]-2,3-dihydro-4H-1,4-benzothiazine-3-one 1-oxide,
6-[4-(4-phenyl-1-piperazinyl)-1-hydroxybutyl]-2,3-dihydro-4H-1,4-benzothiazine-3-one 1-oxide, 6-[5-(4-phenyl-1-piperazinyl)-1-hydroxypentyl]-2,3-dihydro-4H-1,4-benzothiazine-3-one 1-oxide,
6-[6-(4-phenyl-1-piperazinyl)-1-hydroxyhexyl]-2,3-dihydro-4H-1,4-benzothiazine-3-one 1-oxide,
6-[4-(4-phenyl-1-piperazinyl)butyryl]-2,3-dihydro-4H-1,4-benzothiazine-3-one 1,1-dioxide,
6-[5-(4-phenyl-1-piperazinyl)valeryl]-2,3-dihydro-4H-1,4-benzothiazine-3-one 1,1-dioxide,
6-[6-(4-phenyl-1-piperazinyl)caproyl]-2,3-dihydro-4H-1,4-benzothiazine-3-one 1,1-dioxide,
6-[4-(4-phenyl-1-piperazinyl)-1-hydroxybutyl]2,3-dihydro-4H-1,4-benzothiazine-3-one 1,1-dioxide,
6-[5-(4-phenyl-1-piperazinyl)-1-hydroxypentyl]-2,3-dihydro-4H-1,4-benzothiazine-3-one 1,1-dioxide,
6-[6-(4-phenyl-1-piperazinyl)-1-hydroxyhexyl]-2,3-dihydro-4H-1,4-benzothiazine-3-one 1,1-dioxide.

The compounds illustrated above have the general formula [I]wherein Ar is unsubstituted phenyl and the others are as herein defined, but the compounds having the general formula [I]wherein Ar is pyridyl group such as 2- and 4-pyridyl or substituted phenyl such as 2-, 3- and 4-tolyl, 2-, 3- and 4-methoxyphenyl, 2-, 3- and 4-fluorophenyl and 2-, 3- and 4-chlorophenyl and the others are as herein defined are, of course, included in the scope of the present compounds. Among the present compounds, the preferable compounds are as follows.

5-[5-(4-phenyl-1-piperazinyl)valeryl]-2-methoxybenzenesulfonamide,
5-[5-[4-(2-methoxyphenyl)-1-piperazinyl]valeryl]-2-methoxy-benzenesulfonamide,
5-[5-(4-phenyl-1-piperazinyl)valeryl]-2-methylthiobenzenesulfonamide,
5-[5-[4-(2-methoxyphenyl)-1-piperazinyl]valeryl]-2-methylthio-benzenesulfonamide,
5-[5-(4-phenyl-1-piperazinyl)valeryl]-2-methylsulfinyl-benzenesulfonamide,
5-[5-[4-(2-methoxyphenyl)-1-piperazinyl]valeryl]-2-methylsulfinyl-benzenesulfonamide,
5-[5-(4-phenyl-1-piperazinyl)valeryl]-2-methylsulfonyl-benzenesulfonamide,
5-[5-[4-(2-methoxyphenyl)-1-piperazinyl]valeryl]-2-methylsulfonyl-benzenesulfonamide,
5-[5-(4-phenyl-1-piperazinyl)valeryl]salicylamide,
5-[5-[4-(2-methoxyphenyl)-1-piperazinyl]valeryl]-salicylamide,
5-[4-(4-phenyl-1-piperazinyl)butyryl]salicylamide,
5-[4-[4-(2-methoxyphenyl)-1-piperazinyl]butyryl]-salicylamide,
5-[4-[4-(2-pyridyl)-1-piperazinyl)butyryl]-salicylamide,
5-[4-[4-(2-pyridyl)-1-piperazinyl]-1-hydroxybutyl]-salicylamide,
5-[5-(4-phenyl-1-piperazinyl)valeryl]-2-methoxy-N-carbamoylaniline,
5-[5-[4-(2-methoxyphenyl)-1-piperazinyl]valeryl]-2-methoxy-N-carbamoylaniline,
5-[5-(4-phenyl-1-piperazinyl)valeryl]-2-methoxyacetanilide,
5-[5-[4-(2-methoxyphenyl)-1-piperazinyl]valeryl]-2-methoxyacetanilide,
5-[5-(4-phenyl-1-piperazinyl)valeryl]-2-methoxy-N-methanesulfonylaniline,
5-[5-[4-(2-methoxyphenyl)-1-piperazinyl]valeryl]-methoxy-N-methanesulfonylaniline,
5-[5-(4-phenyl-1-piperazinyl)valeryl]-2-hydroxy-N-carbamoylaniline,
5-[5-[4-(2-methoxyphenyl)-1-piperazinyl]valeryl]-2-hydroxy-N-carbamoylaniline,
5-[5-(4-phenyl-1-piperazinyl)valeryl]-2-hydroxyacetanilide,
5-[5-[4-(2-methoxyphenyl)-1-piperazinyl]valeryl]-2-hydroxyacetanilide,
5-[5-(4-phenyl-1-piperazinyl)valeryl]-2-methylthio-N-carbamoylaniline,
5-[5-[4-(2-methoxyphenyl)-1-piperazinyl]valeryl]-2-methylthio-N-carbamoylaniline,
5-[5-(4-phenyl-1-piperazinyl)valeryl]-2-methylthio-acetanilide,
5-[5-[4-(2-methoxyphenyl)-1-piperazinyl]valeryl]-2-methylthio-acetanilide,
5-[5-(4-phenyl-1-piperazinyl)valeryl]-2-methylsulfinyl-N-carbamoylaniline,
5-[5-[4-(2-methoxyphenyl)-1-piperazinyl]valeryl]-2-methylsulfinyl-N-carbamomlaniline,
5-[5-(4-phenyl-1-piperazinyl)valeryl]-2-methylsulfinyl-acetanilide,
5-[5-[4-(2-methoxyphenyl)-1-piperazinyl]valeryl]-methylsulfinyl-acetanilide,
5-[5-(4-phenyl-1-piperazinyl)valeryl]-2-methylsulfonyl-N-carbamoylaniline,
5-[5-[4-(2-methoxyphenyl)-1-piperazinyl]valeryl]-2-methylsulfonyl-N-carbamoylaniline,
5-[5-(4-phenyl-1-piperazinyl)valeryl]-2-methylsulfonyl-acetanilide,
5-[5-[4-(2-methoxyphenyl)-1-piperazinyl]valeryl]-2-methylsulfonyl-acetanilide,
6-[5-(4-phenyl-1-piperazinyl)valeryl]-2,3-dihydro-4H-1,4-benzoxazine-3-one,
6-[5-[4-(2-methoxyphenyl)-1-piperazinyl]valeryl]-2,3-dihydro-4H-1,4-benzoxazine-3-one,
7-[5-(4-phenyl-1-piperazinyl)valeryl]-2,3,4,5-tetrahydro-1,5-benzoxazepine-4-one,
7-[5-[4-(2-methoxyphenyl)-1-piperazinyl]valeryl]-2,3,4,5-tetrahydro-1,5-benzoxazepine-4-one,
6-[5-(4-phenyl-1-piperazinyl)valeryl]-2,3-dihydro-4H-1,4-benzothiazine-3-one,
6-[5-[4-(2-methoxyphenyl)-1-piperazinyl]valeryl]-2,3-dihydro-4H-1,4-benzothiazine-3-one,
6-[5-(4-phenyl-1-piperazinyl)valeryl]-2,3-dihydro-4H-1,4-benzothiazine-3-one 1-oxide,
6-[5-[4-(2-methoxyphenyl)-1-piperazinyl]valeryl]-2,3-dihydro-4H-1,4-benzothiazine-3-one 1-oxide,
6-[5-(4-phenyl-1-piperazinyl)valeryl]-2,3-dihydro-4H-1,4-benzothiazine-3-one 1,1-dioxide,
6-[5-[4-(2-methoxyphenyl)-1-piperazinyl]valeryl]-2,3-dihydro-4H-1,4-benzothiazine-3-one 1,1-dioxide,
5-[5-(4-phenyl-1-piperazinyl)valeryl]-N-ethylsalicylamide,
5-[5-(4-phenyl-1-piperazinyl)valeryl]-N-propylsalicylamide,
5-[5-(4-phenyl-1-piperazinyl)valeryl]-2-hydroxypropionanilide,
5-[5-(4-phenyl-1-piperazinyl)valeryl]-2-hydroxybutyranilide,
5-[5-(4-phenyl-1-piperazinyl)valeryl]-N,N-diethylsalicylamide,
5-[5-(4-phenyl-1-piperazinyl)valeryl]-N,N-dipropylsalicylamide,
5-[5-(4-phenyl-1-piperazinyl)valeryl]-2-hydroxy-N-ethylcarbamoylaniline,
5-[5-(4-phenyl-1-piperazinyl)valeryl]-2-hydroxy-N-propylcarbamoylaniline,
5-[5-(4-phenyl-1-piperazinyl)valeryl]-2-methoxypropionanilide,
5-[5-(4-phenyl-1-piperazinyl)valeryl]-2-methoxybutyranilide, 5-[5-(4-phenyl-1-piperazinyl)valeryl]-2-methoxy-N-ethylcarbamoylaniline,
5-[5-(4-phenyl-1-piperazinyl)valeryl]-2-methoxy-N-propylcarbamoylaniline,
5-[5-(4-phenyl-1-piperazinyl)valeryl]-2-methoxy-N-ethanesulfonylaniline,
5-[5-(4-phenyl-1-piperazinyl)valeryl]-2-methoxy-N-isopropanesulfonylaniline,
5-[5-(4-phenyl-1-piperazinyl)valeryl]-2-methoxy-N-ethylbenzenesulfonamide,
5-[5-(4-phenyl-1-piperazinyl)valeryl]-2-methoxy-N-propylbenzenesulfonamide,
5-[5-(4-phenyl-1-piperazinyl)valeryl]-2-methoxy-N,N-diethylbenzenesulfonamide,
5-[5-(4-phenyl-1-piperazinyl)valeryl]-2-methoxy-N,N-dipropylbenzenesulfonamide,
5-[5-(4-phenyl-1-piperazinyl)valeryl]-2-methylthiopropionanilide,
5-[5-(4-phenyl-1-piperazinyl)valeryl]-2-methylthiobutyranilide,
5-[5-(4-phenyl-1-piperazinyl)valeryl]-2-methylthio-N-ethanesulfonylaniline,
5-[5-(4-phenyl-1-piperazinyl)valeryl]-2-methylthio-N-isopropanesulfonylaniline,
5-[5-(4-phenyl-1-piperazinyl)valeryl]-2-methylthio-N-ethylbenzenesulfonamide,
5-[5-(4-phenyl-1-piperazinyl)valeryl]-2-methylthio-N-propylbenzenesulfonamide,
5-[5-(4-phenyl-1-piperazinyl)valeryl]-2-methylthio-N,N-diethylbenzenesulfonamide,
5-[5-(4-phenyl-1-piperazinyl)valeryl]-2-methylthio-N,N-dipropylbenzenesulfonamide,
5-[5-(4-phenyl-1-piperazinyl)valeryl]-2-methylsulfinylpropionanilide,
5-[5-(4-phenyl-1-piperazinyl)valeryl]-2-methylsulfinylbutyranilide,
5-[5-(4-phenyl-1-piperazinyl)valeryl]-2-methylsulfinylethanesulfonylaniline,
5-[5-(4-phenyl-1-piperazinyl)valeryl]-2-methylsulfinylisopropanesulfonylaniline,
5-[5-(4-phenyl-1-piperazinyl)valeryl]-2-methylsulfinyl-N-ethylbenzenesulfonamide,
5-[5-(4-phenyl-1-piperazinyl)valeryl]-2-methylsulfinyl-N-propylbenzenesulfonamide,
5-[5-(4-phenyl-1-piperazinyl)valeryl]-2-methylsulfinyl-N,N-diethylbenzenesulfonamide,
5-[5-(4-phenyl-1-piperazinyl)valeryl]-2-methylsulfinyl-N,N-dipropylbenzenesulfonamide,
5-[5-(4-phenyl-1-piperazinyl)valeryl]-2-methylsulfonylpropionanilide,
5-[5-(4-phenyl-1-piperazinyl)valeryl]-2-methylsulfonylbutyranilide,
5-[5-(4-phenyl-1-piperazinyl)valeryl]-2-ethoxybenzenesulfonamide,
5-[5-(4-phenyl-1-piperazinyl)valeryl]-2-propoxybenzenesulfonamide,
5-[5-(4-phenyl-1-piperazinyl)valeryl]-2-ethylthiobenzenesulfonamide,
5-[5-(4-phenyl-1-piperazinyl)valeryl]-2-propylthiobenzenesulfonamide,
5-[5-(4-phenyl-1-piperazinyl)valeryl]-2-ethylsulfinylbenzenesulfonamide,
5-[5-(4-phenyl-1-piperazinyl)valeryl]-2-propylsulfinylbenzenesulfonamide.

The present invention also relates to the physiologically acceptable acid addition salt of the present compound of the general formula [I]. Such salts include those derived from organic and inorganic acids such as, without limitation, hydrochloric acid, hydrobromic acid, sulfuric acid, phosphoric acid, nitric acid, acetic acid, succinic acid, adipic acid, propionic acid, tartaric acid, fumaric acid, maleic acid, oxalic acid, citric acid, benzoic acid, toluenesulfonic acid, methanesulfonic acid and the like.

According to the present invention, the foregoing compounds can be prepared by reacting halogeno-alkanoylbenzene or halogeno-alkylbenzene of the formula [II]:

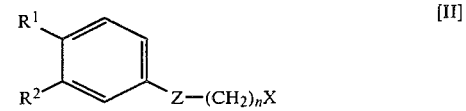

wherein $R^1$, $R^2$, Z and n are as herein defined and $X$ is a halogen atom, with piperazine of the formula [III]:

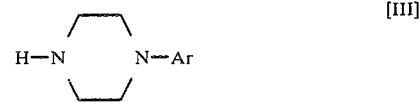

wherein Ar is as herein defined.

That is, ω-halogenoalkanoyl benzene of the formula [II']:

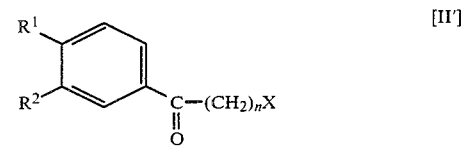

wherein $R^1$, $R^2$, n and X are as herein defined, with piperazine of the formula [III] to obtain ω-piperazinylalkanoylbenzene having the general formula [I] wherein Z is

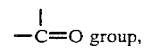

i.e. the formula [I']:

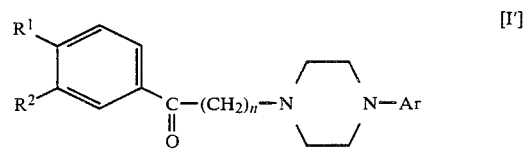

wherein $R^1$, $R^2$, n and Ar are as herein defined, and optionally reducing the carbonyl group in the thus-obtained compound of the formula [I'] to obtain ω-piperazinyl-α-hydroxyalkylbenzene having the general formula [I] wherein Z is —CH(OH)— group, i.e. the formula [I'']:

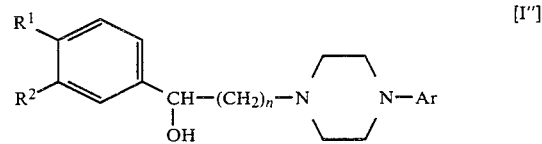

wherein R¹, R², n and Ar are as herein defined.

Alternatively, the compound of the formula [I''] may be prepared by reacting ω-halogeno-α-hydroxyalkyl-benzene of the formula [II'']:

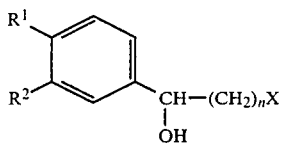

wherein R¹, R², n and X are as herein defined, with piperazine of the formula [III]. The compound of the formula [II''] used as the starting material is easily obtained by reducing the carbonyl group in ω-halogenoalkanoyl benzene of the formula [II'].

In the above reaction, equimolecular amounts of the compound of the formula [II]and piperazine of the formula [III]are used. However, to proceed the reaction smoothly it is preferable to use piperazine in excess. Generally, piperazine is used in an amount of 1 to 10 moles with respect to 1 mole of the compound of the formula [II].

The reaction can be carried out without the presence of a solvent, but to proceed the reaction smoothly, it is preferable to react in an inert solvent such as water, dioxane, tetrahydrofuran, dimethyl formamide, dimethyl sulfoxide, lower alcohol or the like, or a mixture thereof.

The reaction temperature is not particularly limited and is generally in the range of between room temperature and about 150° C.

The reaction time is of course varied depending on the reaction temperature, the reactivity of each starting material and the kind of the solvent used, but is usually in the range of between 10 minutes and 20 hours.

It is advisable for proceeding smoothly the reaction to use the scavenger for hydrogen halide produced in the course of the reaction. Such scavengers include, without limitation, inorganic salts such as potassium hydroxide, sodium hydroxide, potassium carbonate, sodium carbonate, sodium hydrogen carbonate and the like, tertiary organic amines such as pyridine, triethylamine and the like, and so on. If the scavenger is used, its used amount is generally 1 to 5 moles with respect to 1 mole of piperazine.

When the compound of the general formula [I] wherein R¹ is hydroxy group and the others are as herein defined is desired, it is preferable to carry out the above reaction while protecting the hydroxy group, as shown as follows.

ω-halogenoalkanoyl benzene of the formula [IV]:

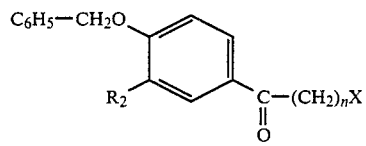

wherein R², n and X are as herein defined, is reacted with piperazine of the formula [III] to prepare ω-piperazinylalkanoylbenzene of the formula [V]:

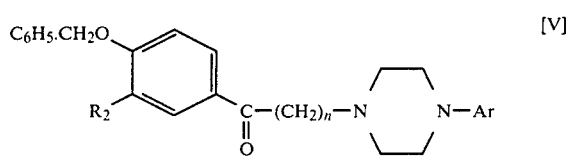

wherein R², n and Ar are as herein defined, and then the thus prepared compound of the formula [VI] is subjected to hydrogenolysis of the benzyl group in the presence of catalyst such as palladium-carbon directly. Alternatively, it is possible to reduce the benzyl group in the compound of the formula [V] at the time simultaneous with or before the reduction of the carbonyl group to obtain the compound of the general formula [I] wherein R¹ is hydroxy group, Z is

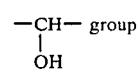

and the others are as herein defined. The compound of the formula [IV] used as the starting material in the above reaction is prepared in accordance with any conventional method, for example, by reacting the compound of the formula [II'] wherein R¹ is hydroxy group and the others are as herein defined, with benzyl halide such as benzyl bromide and benzyl chloride in a solvent such as water, lower alcohol, tetrahydrofuran, dioxane, dimethyl formamide, dimethyl sulfoxide and the like in the presence of potassium hydroxide, sodium hydroxide, potassium alkoxide, sodium alkoxide, sodium hydride and the like.

After the conclusion of the reaction, the product is purified in accordance with any conventional purification method.

And, the acid addition salt of the present compound may be prepared by neutralizing the compound of the formula [I] with the desired acid in accordance with the conventional method.

The present compounds including the acid addition salt thereof show the ability to reduce blood pressure and a low acute toxicity, as will be shown in Examples. Accordingly, the present compounds are highly desirable as pharmaceutical agents to be used in the treatment of hypertension.

Pharmaceutical compositions for effecting such treatment will contain at least one of the present compound in combination with a pharmaceutical carrier which is nontoxic, inert and pharmaceutically acceptable. Other pharmaceutically active ingredients may be incorporated in the composition. Such pharmaceutical compositions are preferably in dosage unit form.

Although the dosage must in each case be carefully adjusted considering the age, weight and condition of the recipient, the route of administration, the nature and gravity of the illness, the kinds and frequency of the other treatment if any, generally the daily dose will be from 0.1 to 100 mg/kg of body weight. The preferable daily dose is 1 to 30 mg/kg of body weight. In some instances a sufficient therapeutic effect can be obtained at lower doses while in others, larger doses will be required.

Oral administration can be effected utilizing solid and liquid dosage unit forms such as powders, tablets, dragees, capsules, granulates, suspension, solutions, syrups and the like.

Oral solids such as powders, tablets and so on can be prepared in dosage unit form so as to contain 5 to 95% by weight, preferably 25 to 90% by weight, that is, 5 to 500 mg, preferably 25 to 250 mg of the present compound as an active ingredient.

Powders are prepared by comminuting the present compound to a suitable fine size and mixing with a similarly comminuted pharmaceutical solid carrier such as starch, lactose, sucrose, glucose or mannitol. Any conventional adjuvants such as sweetening, flavoring, preservative, dispersing and coloring agents can also be present.

Capsules are made by preparing a powder mixture as described above and filling formed gelatin sheaths. The adjuvants mentioned above can also be added to the powder mixture before the filling operation and other adjuvants such as a disintegrating or solubilizing agent to improve the availability of the medicament when the capsule is ingested may be added.

Tablets are formulated for example by preparing a powder mixture, granulating, adding any adjuvants and pressing into tablets.

Oral fluids such as solutions, syrups, suspensions and so on can be prepared in dosage unit form so as to contain 0.5 to 10% by weight of the present compound as an active ingredient. Suspensions can be formulated by dispersing the present compound in a nontoxic pharmaceutical liquid carrier. Any conventional adjuvants such as solubilizers, emulsifiers, preservatives, flavor and the like can also be present.

Parenteral administration can be effected utilizing liquid dosage forms such as sterile solutions and suspensions intended for subcutaneous, intramuscular, intravenous or intraperitoneal injection. These are prepared by suspending or dissolving a measured amount of the present compound in a nontoxic liquid vehicle suitable for injection such as a physiological saline solution, solution of sucrose such as dextrose and the like, solution of glycols such as propylene glycol and ethylene glycol. Especially, the injection including physiological saline solution as the carrier contains preferably 0.5 to 20% by weight, more preferably 1 to 10% by weight of the present compound as the active ingredient.

The following examples will serve to further understand the present invention through the presentation of specific embodiments. These examples should not be construed as a limitation on the scope of the invention since the subject matter regarded as the invention is set forth in the appended claims.

EXAMPLE 1

5-[5-[4-(2-methoxyphenyl)-1-piperazinyl]valeryl]-2-methoxy-benzenesulfonamide dihydrochloride (Compound No. 2)

A mixture of 2.6 g of 5-(5-chlorovaleryl)-2-methoxy-benzenesulfonamide, 1.8 g of 1-(2-methoxyphenyl)piperazine, 1 g of sodium carbonate and 20 ml of dimethyl sulfoxide was stirred at 90° C. for 3 hours. After the reaction was finished, water was added to the reaction mixture and then the mixture was extracted with ethyl acetate. The extract was washed with water saturated with sodium chloride and dried over anhydrous sodium sulfate. The solvent was distilled away and the residue was dissolved in acetone followed by adding concentrated hydrochloric acid in required amount to produce crystals. The thus-produced crystals were recrystallized from methanol to obtain 2.8 g of the titled compound (yield: 61%).

The characteristics of this compound were shown in Table 1.

In the similar manner, 5-[5-[4-(2-chlorophenyl)-1-piperazinyl] valeryl]-2-methoxy-benzenesulfonamide dihydrochloride (Compound No. 4) was prepared, whose characteristics being also shown in Table 1.

EXAMPLE 2

5-[5-[4-(2-methoxyphenyl)-1-piperazinyl]valeryl]-2-methylthio-benzenesulfonamide (Compound No. 6)

A mixture of 5 g of 5-(5-chlorovaleryl)-2-methylthio-benzenesulfonamide, 3.4 g of 1-(2-methoxyphenyl)piperazine, 2.0 g of sodium carbonate and 25 ml of dimethyl sulfoxide was heated at 90° C. for 6 hours while stirring. After the reaction was finished, 100 ml of water and 100 ml of ethyl acetate were added to the reaction mixture and the stirring was continued for 30 minutes to produce crystals. The thus-produced crystals was filtered off to obtain 6.0 g of the titled compound (yield: 80.5%).

The characteristics of this compound were shown in Table 1.

In the similar manner, 5-[5-(4-phenyl-1-piperazinyl)-valeryl]-2-methoxy-benzenesulfonamide (Compound No. 1), 5-[5-[4-(2-methylphenyl)-1-piperazinyl]valeryl]-2-methoxy-benzenesulfonamide (Compound No. 3) and 5-[5-(4-phenyl-1-piperazinyl)valeryl]-2-methylthio-benzenesulfonamide (Compound No. 5) were prepared, whose characteristics being also shown in Table 1.

EXAMPLE 3

5-[5-[4-(2-methoxyphenyl)-1-piperazinyl]valeryl]-2-methylsulfinyl-benzenesulfonamide (Compound No. 7)

0.9 Gram of the compound obtained in Example 2 was dissolved in 15 ml of acetic acid and 0.33 ml of an aqueous 30% hydrogen peroxide solution was added thereto and the stirring was continued at room temperature for 3 hours. After the reaction was finished, an aqueous sodium sulfite solution in an appropriate amount was added followed by concentrating under reduced pressure. The thus-produced residue was dissolved in chloroform and potassium carbonate was added and then the stirring was continued for 30 minutes. The chloroform solvent was distilled away and the residue was purified by chromatography (adsorbent: silica gel, eluent: 4% methanol-chloroform) to produce crystals. The crude crystals were recrystallized from acetone-ether to obtain 0.6 g of the titled compound (yield: 64.5 %).

The characteristics of this compound were shown in Table 1.

EXAMPLE 4

5-[4-[4-(2-pyridyl)-1-piperadinyl]butyryl]-2-methoxy-benzenesulfonamide (Compound No. 9)

A mixture of 1.9 g of 5-(4-chlorobutyryl)-2-methoxy-benzenesulfonamide, 1.2 g of 4-(2-pyridyl)-1-piperazine, 1.8 ml of triethylamine and 10 ml of dimethyl sulfoxide was heated at 80° C. for 6 hours while stirring. After the reaction was finished, water was added to the reaction mixture and the mixture was extracted with ethyl acetate. The extract was washed with water saturated with sodium chloride and dried over anhydrous sodium sulfate. The solvent was distilled away and the residue was purified by chromatography (adsorbent: silica gel, eluent: 4% methanol-chloroform) followed by crystallizing from ethyl acetate to obtain 1.5 g of the titled compound (yield: 55.3%). The characteristics of this compound were shown in Table 1.

EXAMPLE 5

5-[4-[4-(2-pyridyl)-1-piperazinyl]-1-hydroxybutyl]-2-methoxy-benzenesulfonamide dihydrochloride (Compound No. 10)

0.8 Gram of the compound obtained in Example 4 was dissolved in 8 ml of ethanol and 70 mg of sodium borohydride was added thereto and then the stirring was continued for 3 hours. After the reaction was finished, the reaction mixture was concentrated, extracted with chloroform, washed with water saturated with sodium chloride and dried over anhydrous sodium sulfate. After distilling away the solvent, the residue was dissolved in acetone and 0.21 ml of concentrated hydrochloric acid was added thereto to produce an oily product. The thus-produced product was crystallized from ethanolacetone to obtain 0.7 g of the titled compound (yield: 87.1%).

The characteristics of this compound were shown in Table 1.

In the similar manner, 5-[5-(4-phenyl-1-piperazinyl)-1-hydroxypentyl]-2-methylthio-benzenesulfonamide (Compound No. 8) was prepared, whose characteristics being also shown in Table 1.

EXAMPLE 6

5-[5-(4-phenyl-1-piperazinyl]valeryl]-salicylamide (Compound No. 11)

A mixture of 2 g of 5-(5-chlorovaleryl)-2-benzyloxy-benzamide, 1 g of 1-phenylpiperazine, 0.6 g of sodium carbonate and 10 ml of dimethyl sulfoxide was heated at 90° C. for 6 hours while stirring. After the reaction was finished, water was added to the reaction mixture and the mixture was extracted with ethyl acetate. The extract was washed with water saturated with sodium chloride, dried over anhydrous sodium sulfate and concentrated. The thus produced residue was dissolved in acetone and concentrated hydrochloric acid in an amount of 2 equivalents was added thereto to produce crystals. The crystals were filtered off to obtain 2.3 g of 5-[5-(4-phenyl-1-piperazinyl)valeryl]-2-benzyloxy-benzamide (yield: 73%).

1.7 Gram of this benzamide was liberated in an aqueous potassium carbonate solution, extracted with chloroform, dried over anhydrous sodium sulfate and concentrated. The thus-produced residue was dissolved in 50 ml of ethanol and then the solution was subjected to hydrogenolysis on 500 mg of 5% Pd - C. After the reaction was finished, the precipitated crystals were dissolved in hot methanol and the catalyst was filtered off. Then the solvent was distilled away and the residue was crystallized from ethanol to obtain 1.0 g of the titled compound. The characteristics of this compound were shown in Table 1. And, IR spectrum of this compound was shown in FIG. 1 of the accompanying drawings.

In the similar manner, 5-[5-[4-(2-chlorophenyl)-1-piperazinyl]valeryl]salicylamide (Compound No. 13), 5-[5-[4-(2-pyridyl)-1-piperazinyl]valeryl]salicylamide (Compound No. 14), 5-[5-[4-(2-pyridyl)-1-piperazinyl]-valeryl]-salicylic acid (Compound No. 15) and 5-[5-[4-(2-methoxyphenyl)-1-piperazinyl]valeryl]salicylic acid (Compound No. 16) were prepared, whose characteristics being also shown in Table 1.

EXAMPLE 7

5-[4-(4-phenyl-1-piperazinyl)-1-hydroxybutyl]-salicylamide dihydrochloride (Compound No. 22)

A mixture of 1 g of 5-(4-chlorobutyryl)-2-benzyloxy-benzamide, 1.2 g of 1-phenylpiperazine, 3.3 ml of triethylamine and 10 ml of dimethyl sulfoxide was heated at 90° C. for 15 hours while stirring. After the reaction was finished, water was added to the reaction mixture and the mixture was extracted with ethyl acetate. The extract was washed with water saturated with sodium chloride, dried over anhydrous sodium sulfate and concentrated. The thus-produced residue was crystallized from ethyl acetate-ether to obtain 1.6 g of 5-[4-(4-phenyl-1-piperazinyl)butyryl]-2-benzyloxy-salicylamide (yield: 58.0%).

1.1 Gram of this salicylamide was dissolved in 20 ml of dioxane and 20 ml of ethanol and 90 mg of sodium borohydride was added thereto to react at room temperature for 4 hours. After the reaction was finished, the solvent was distilled away and the residue was extracted with ethyl acetate after adding water. The extract was washed with water saturated with sodium chloride, dried over anhydrous sodium sulfate and concentrated. The thus-produced residue was crystallized from ether to obtain 0.9 g of 5-[4-(4-phenyl-1-piperazinyl)-1-hydroxybutyl]-2-benzyloxy-salicylamide (yield: 81%).

Figure 2:
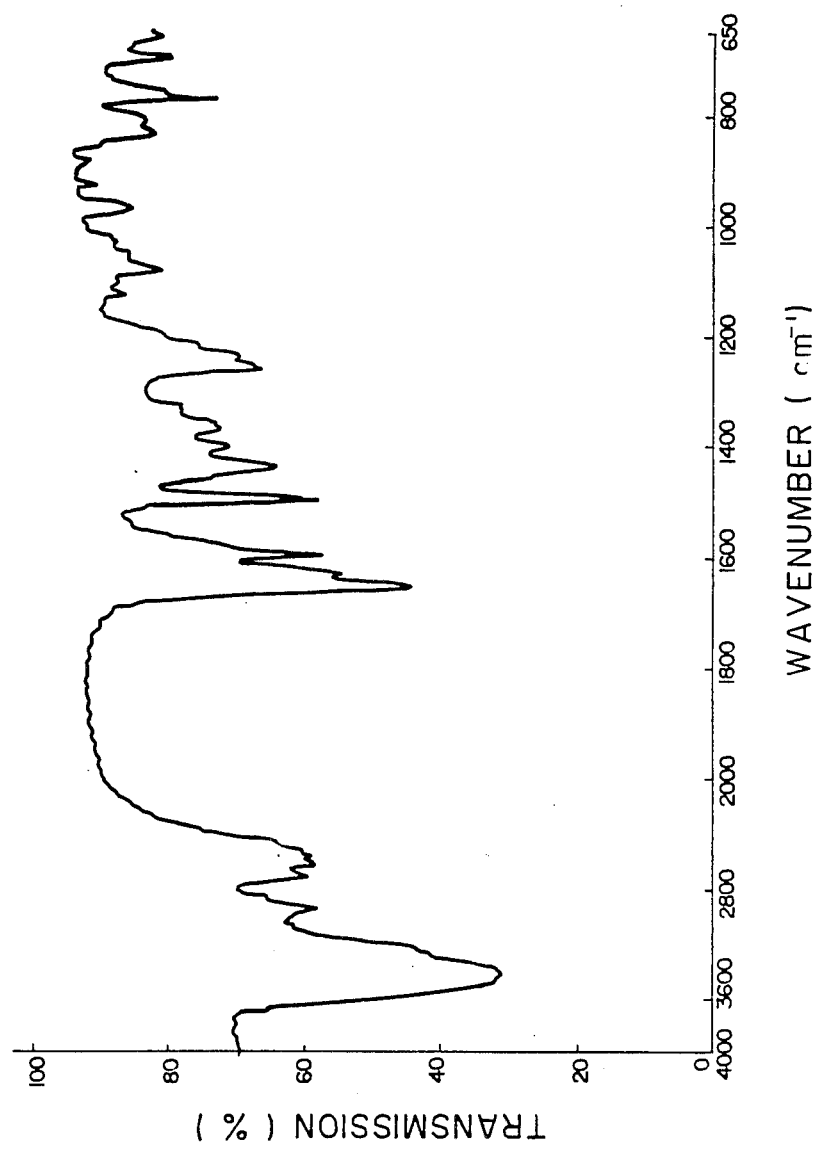

0.8 Gram of this salicylamide was suspended in 50 ml of methanol and 10 ml of dioxane and then the suspension was subjected to hydrogenolysis on 0.3 g of 5% Pd - C. After the reaction was finished, the catalyst was removed and the solvent was distilled away to produce an oily product. The produced product was dissolved in acetone and then concentrated hydrochloric acid in an amount of 2 equivalents was added thereto followed by decanting the solvent and crystallizing from ethanolacetone to obtain 0.6 g of the titled compound (yield: 76%). The characteristics of this compound were shown in Table 1. And, IR spectrum of this compound was shown in FIG. 2 of the accompanying drawings.

In the similar manner, 5-[5-[4-(2-pyridyl)-1-piperazinyl]-1-hydroxypentyl]salicylic acid (Compound No. 17) and 5-[4-[4-(2-pyridyl)-1-piperazinyl]-1-hydroxybutyl]-salicylamide (Compound No. 21) were prepared, whose characteristics being also shown in Table 1.

EXAMPLE 8

5-[4-[4-(2-pyridyl)-1-piperazinyl]butyryl]-salicylamide (Compound No. 18)

2.5 Gram of 5-[4-[4-(2-pyridyl)-1-piperazinyl]-butyryl]-2-benzyloxy-benzamide was obtained from 3 g of 5-(4-chlorobutyryl)-2-benzyloxy-benzamide in a similar manner to Example 7 (yield: 60.6%).

2.3 Gram of this benzamide was dissolved in 100 ml of ethanol and then subjected to hydrogenolysis according to the method described in Example 6 to obtain 1.2 g of the titled compound (yield: 65%).

The characteristics of this compound were shown in Table 1.

Figure 3:
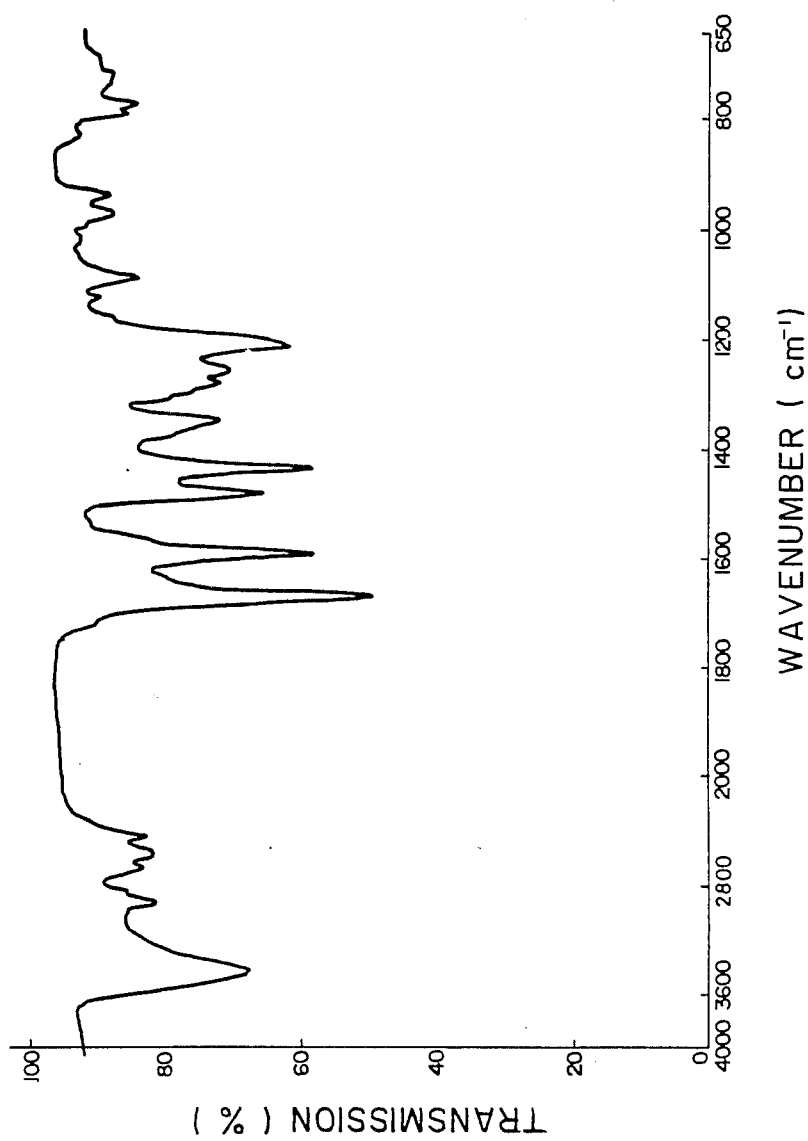
Figure 4:
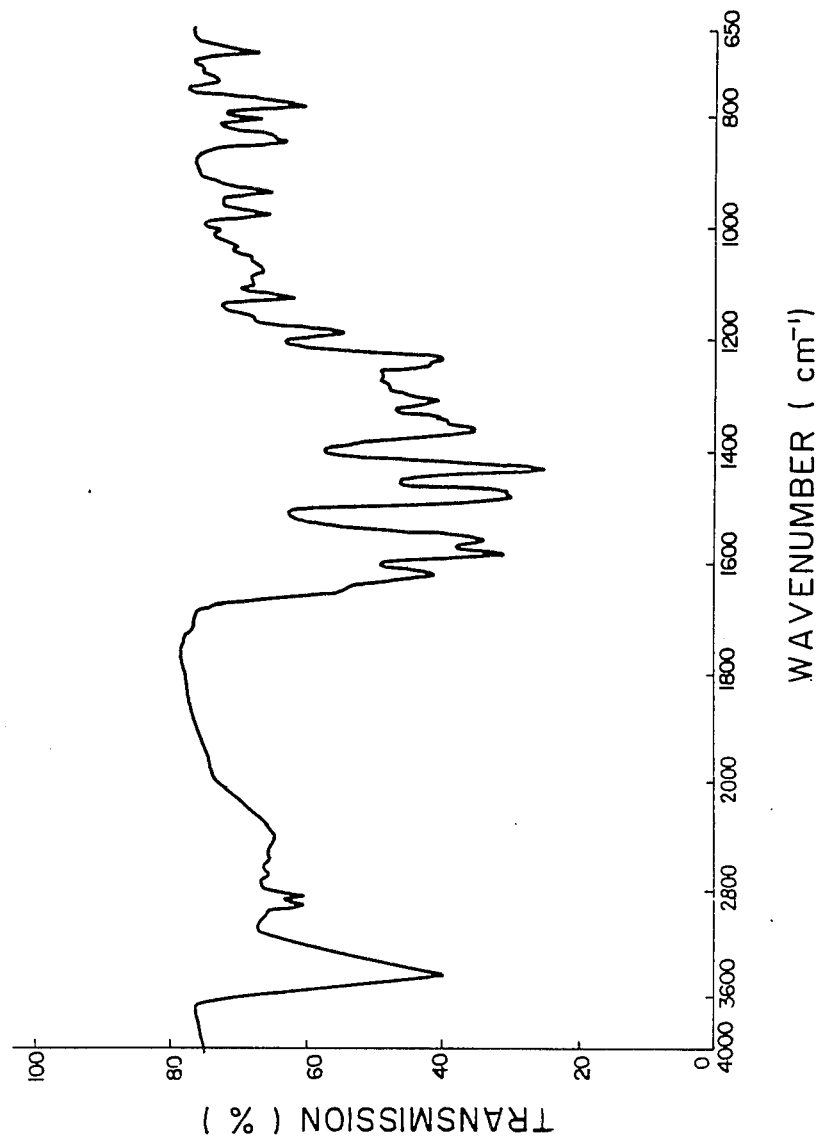

In the similar manner, methyl 5-[4-[4-(2-pyridyl)-1-piperazinyl]butyryl]salicylate (Compound No. 19) and 5-[4-[4-(2-pyridyl)-1-piperazinyl]butyryl]salicylic acid (Compound No. 20) were prepared, whose characteristics being also shown in Table 1. And, IR spectrum of each compound was shown in FIG. 3 (Compound No. 19) and FIG. 4 (Compound No. 20) of the accompanying drawings.

EXAMPLE 9

5-[5-[4-(2-methoxyphenyl)-1-piperazinyl]valeryl]-salicylamide (Compound No. 12)

A mixture of 1.5 g of 5-(4-chlorovaleryl) 1.4 g of 4-(2-methoxyphenyl)piperazine, 0.7 g of sodium carbonate and 10 ml of dimethyl sulfoxide was heated at 90° C. for 3 hours while stirring. After the reaction was finished, the solvent was distilled away under reduced pressure to produce a residue. Water was added to the residue to dissolve. After washing with ether, the solution was neutralized to pH 6 to 7 with 2N hydrochloric acid to produce crystals. The crystals were filtered off and recrystallized from acetone to obtain 1.2 g of the titled compound (yield: 48%).

The characteristics of this compound were shown in Table 1.

EXAMPLE 10

5-[5-[4-(2-methoxyphenyl)-1-piperazinyl]valeryl]-2-methylthio-N-carbamoylaniline (Compound No. 34)

Figure 5:
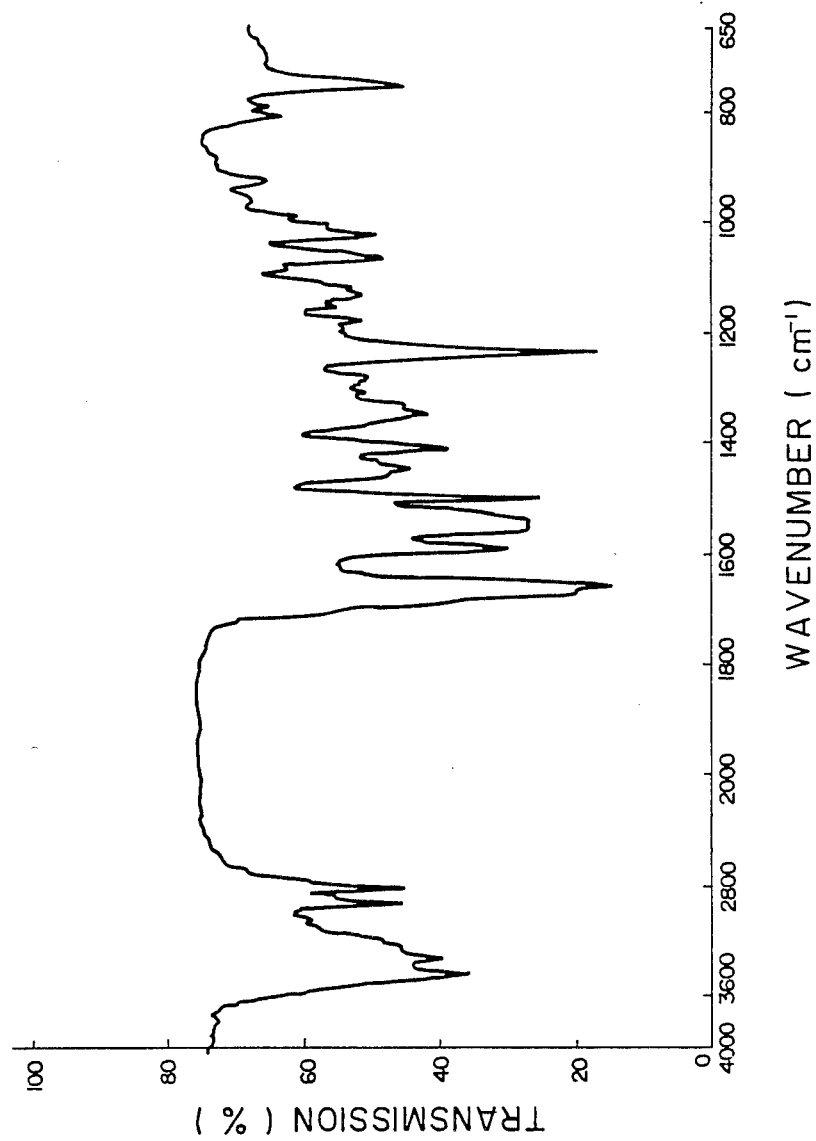

A mixture of 6 g of 5-(5-chlorovaleryl)-2-methylthio-N-carbamoylaniline, 4.2 g of sodium carbonate, 4.6 g of 4-(2-methoxyphenyl)-1-piperazine and 50 ml of dimethyl sulfoxide was heated at 90° C. for 4 hours while stirring. After the reaction was finished, water was added to the reaction mixture and the stirring was continued. The produced crystals were filtered off and recrystallized from ethanol - ethyl acetate to obtain 5.7 g of the titled compound (yield: 62.6%). The characteristics of this compound were shown in Table 1. And, IR spectrum of this compound was shown in FIG. 5 of the accompanying drawings.

Figure 6:
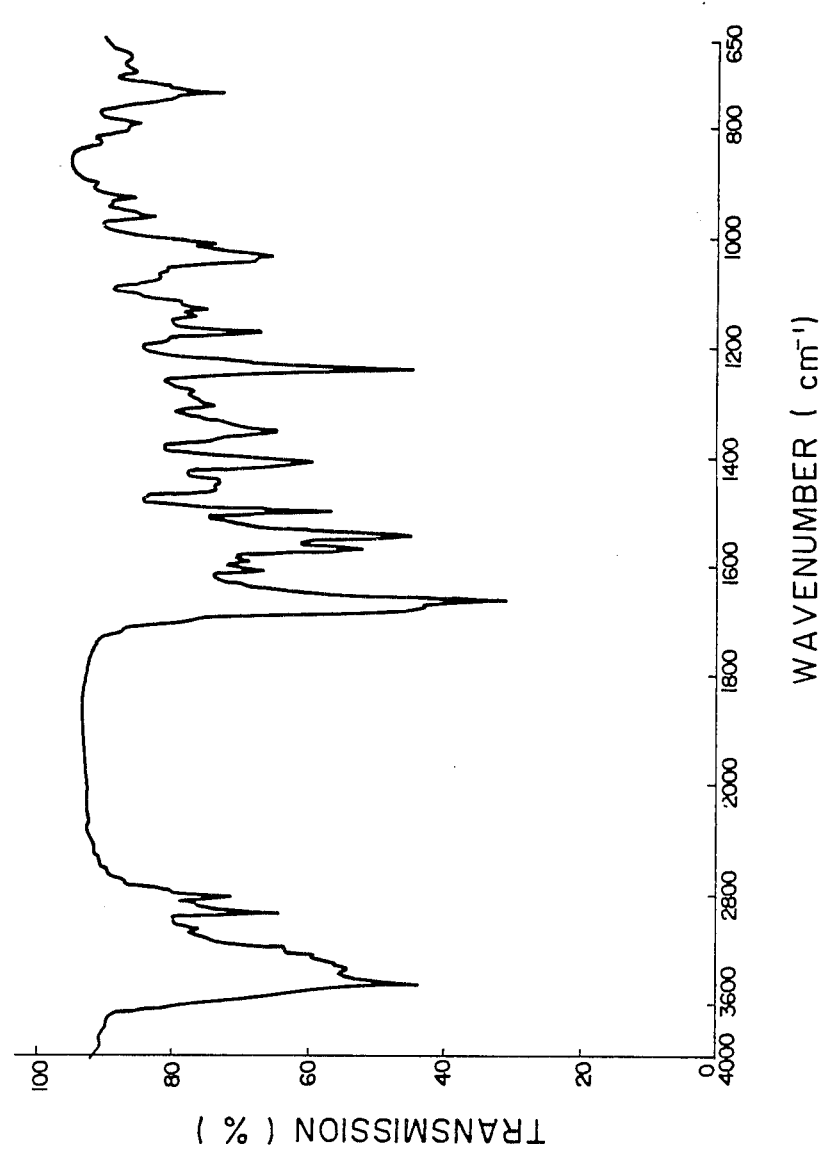

In the similar manner,

5-[5-[4-(2-methoxyphenyl)-1-piperazinyl]valeryl]-2-methoxyacetanilide (Compound No. 24), 5-[5-(4-phenyl-1-piperazinyl)valeryl]-2-methoxy-N-carbamoylaniline (Compound No. 25), 5-[5-[4-(2-methoxyphenyl)-1-piperazinyl]valeryl]-2-methoxy-N-carbamoylaniline (Compound No. 26), 5-[5-[4-(2-chlorophenyl)-1-piperazinyl]valeryl]-2-methoxy-N-carbamoylaniline (Compound No. 27), 5-[5-[4-(2-methylphenyl)-1-piperazinyl]valeryl]-2-methoxy-N-carbamoylaniline (Compound No. 28), 5-[5-[4-(2-methoxyphenyl)-1-piperazinyl]valeryl]-2-methoxy-N-methanesulfonylaniline dihydrochloride (Compound No. 29), 5-[5-[4-(2-methoxyphenyl)-1-piperazinyl]valeryl]-2-methylthio-acetanilide (Compound No. 30), 5-[5-[4-(2-methoxyphenyl)-1-piperazinyl]valeryl]-2-methylsulfinyl-acetanilide (Compound No. 31), 5-[5-[4-(2-methoxyphenyl)-1-piperazinyl]valeryl]-2-methylsulfonyl-acetanilide (Compound No. 32), 5-[5-(4-phenyl-1-piperazinyl)valeryl]-2-methylthio-N-carbamoylaniline (Compound No. 33), 5-[5-[4-(2-methoxyphenyl)-1-piperazinyl]valeryl]-2-methylsulfinyl-N-carbamoylaniline (Compound No. 35), 6-[5-[4-(2-methoxyphenyl)-1-piperazinyl]valeryl]-2,3-dihydro-4H-1,4-benzothiazine-3-one (Compound No. 37), 6-[5-[4-(2-methoxyphenyl)-1-piperazinyl]valeryl]-2,3-dihydro-4H-1,4-benzothiazine-3-one 1-oxide (Compound No. 38), 6-[5-[4-(2-methoxyphenyl)-1-piperazinyl]valeryl]-2,3-dihydro-4H-1,4-benzothiazine-3-one 1,1-dioxide (Compound No. 39), 6-[5-[4-(2-methoxyphenyl)-1-piperazinyl]valeryl]-2,3-dihydro-4H-1,4-benzoxazine-3-one (Compound No. 40) and 7-[5-[4-(2-methoxyphenyl)-1-piperazinyl]valeryl]-2,3,4,5-tetrahydro-1,5-benzoxazepine-4-one (Compound No. 41) were prepared, whose characteristics being also shown in Table 1. And, IR spectrum of the compound (Compound No. 35) was shown in FIG. 6 of the accompanying drawings.

EXAMPLE 11

5-[5-[4-(2-methoxyphenyl)-1-piperazinyl]valeryl]-2-hydroxy-N-carbamoylaniline (Compound No. 36)

2.7 Grams of 5-[5-[4-(2-methoxyphenyl)-1-piperazinyl]valeryl]-2-benzyloxy-N-carbamoylaniline was obtained by preparing in the similar manner to Example 10 from 2.6 g of 5-(5-chlorovaleryl)-2-benzyloxy-N-carbamoylaniline and 1.5 g of 4-(2-methoxyphenyl)-1-piperazine and crystallizing from ethanol (yield: 72.6%).

Figure 7:
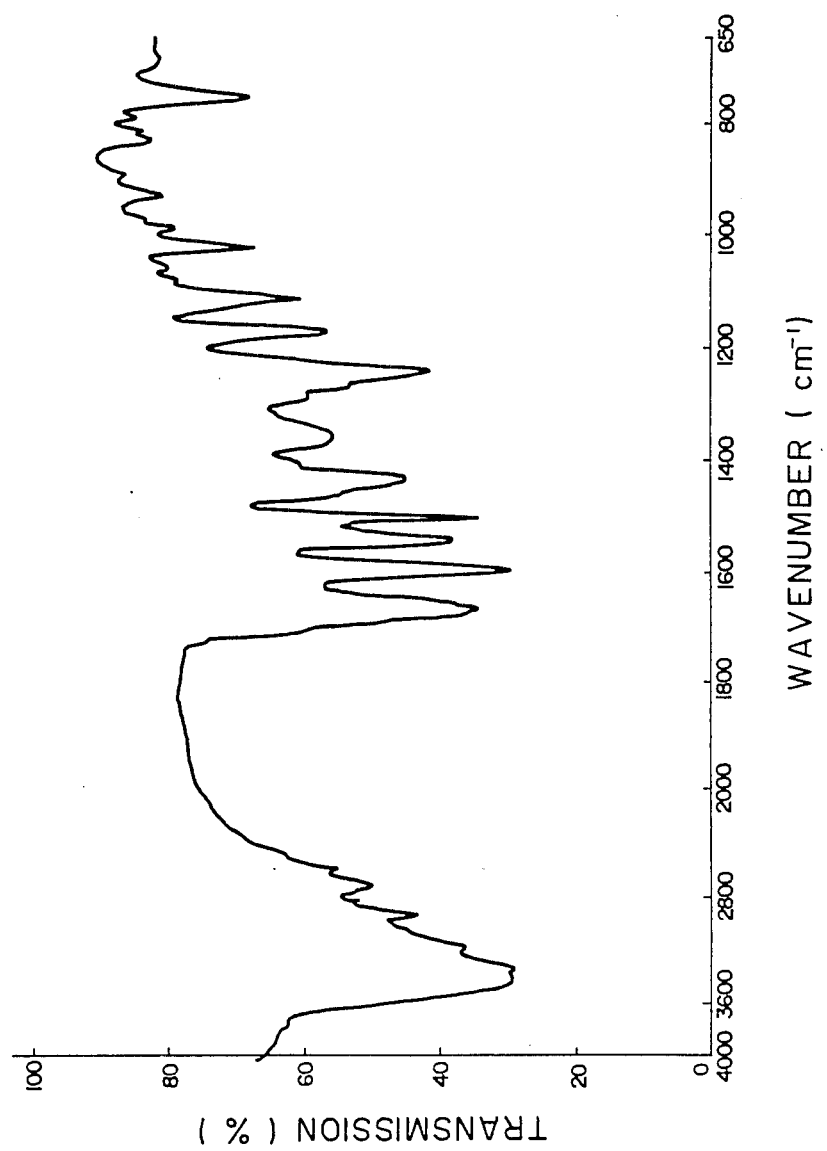

1.9 Gram of this aniline was suspended in 100 ml of ethanol and subjected to hydrogenolysis on 700 mg of 5% Pd - C. The catalyst was removed and the solvent was concentrated followed by crystallizing from acetone to obtain 1.1 g of the titled compound (yield: 70.1%). The characteristics of this compound were shown in Table 1. And, IR spectrum of this compound was shown in FIG. 7 of the accompanying drawings.

In the similar manner, 5-[5-[4-(2-methoxyphenyl)-1-piperazinyl]valeryl]-2-hydroxyacetanilide (Compound No. 23) and 5-[4-[4-(2-pyridyl)-1-piperazinyl]butyryl]-2-hydroxyacetanilide (Compound No. 46) were prepared, whose characteristics being also shown in Table 1.

EXAMPLE 12

6-(2-pyridyl)-1-piperazinyl]butyryl]-2,3-dihydro-4H-1,4-benzothiazine-3-one (Compound No. 49)

A mixture of 2.0 g of 6-(4-chlorobutyryl)-2,3-dihydro-4H-1,4-benzothiazine-3-one, 1.5 g of 4-(2-pyridyl)-1-piperazine, 2.2 ml of triethylamine and 10 ml of dimethyl sulfoxide was heated at 80° C. for 5 hours while stirring. After the reaction was finished, the reaction mixture was extracted with ethyl acetate. The extract was dried over anhydrous sodium sulfate and the solvent was distilled away followed by crystallizing from ethyl acetate-ether to obtain 1.5 g of the titled compound (yield: 50.3%).

The characteristics of this compound were shown in Table 1.

Figure 8:
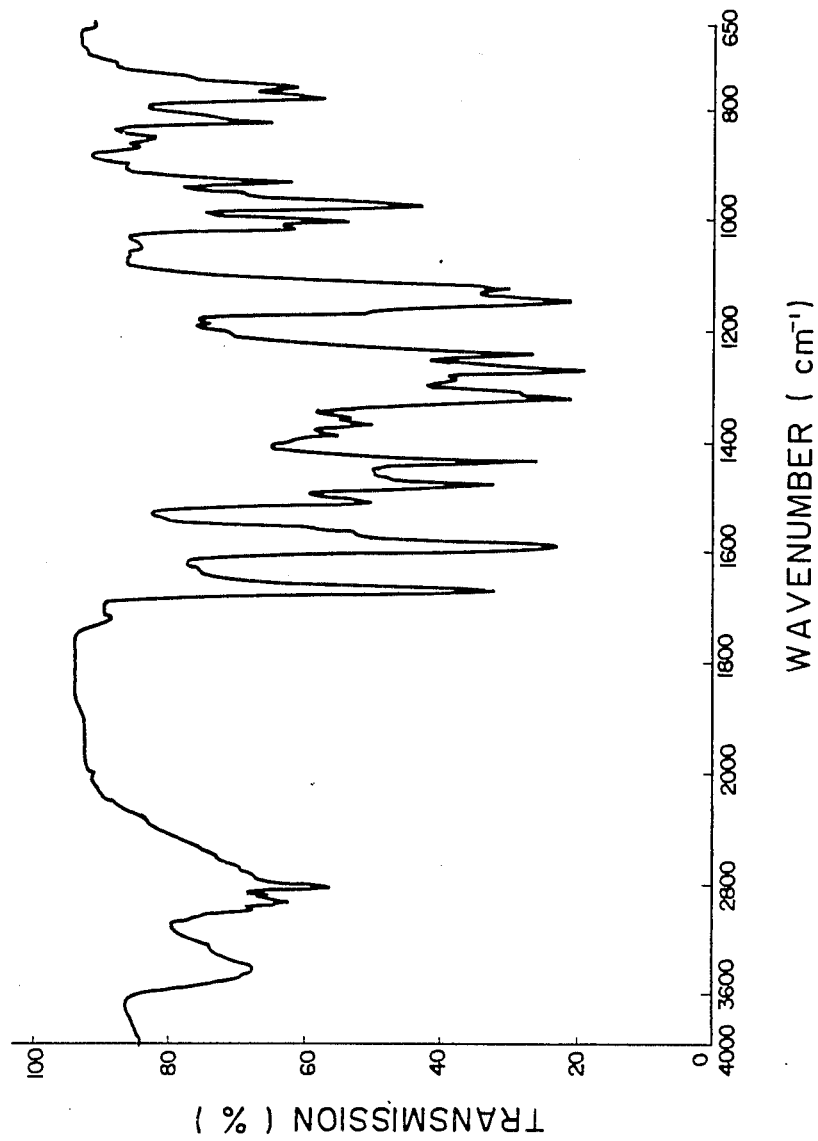

In the similar manner, 5-[4-[4-(2-pyridyl)-1- piperazinyl]butyryl]-2-methoxy-N-carbamoylaniline (Compound No. 42), 5-[4-[4-(2-pyridyl)-1-piperazinyl]butyryl]-2-methoxy-N-methanesulfonylaniline (Compound No. 44) and 5-[4-(4-phenyl-1-piperazinyl)-butyryl]-2-methoxy-N-carbamoylaniline (Compound No. 51) were prepared, whose characteristics being also shown in Table 1. And, IR spectrum of the compound (Compound No. 44) was shown in FIG. 8 of the accompanying drawings.

EXAMPLE 13

6-[4-[4-(2-pyridyl)-1-piperazinyl]-1-hydroxybutyl]-2,3-dihydro-4H-1,4-benzothiazine-3-one (Compound No. 50)

1.0 Gram of the compound obtained in Example 12 was dissolved in 50 ml of ethanol and 180 mg of sodium borohydride was added thereto and further the stirring was continued for 3 hours. After the reaction was finished, 10 ml of water was added and concentrated to half. The produced crystals were filtered off to obtain 0.7 g of the titled compound (yield: 69.6%).

The characteristics of this compound were shown in Table 1.

Figure 9:
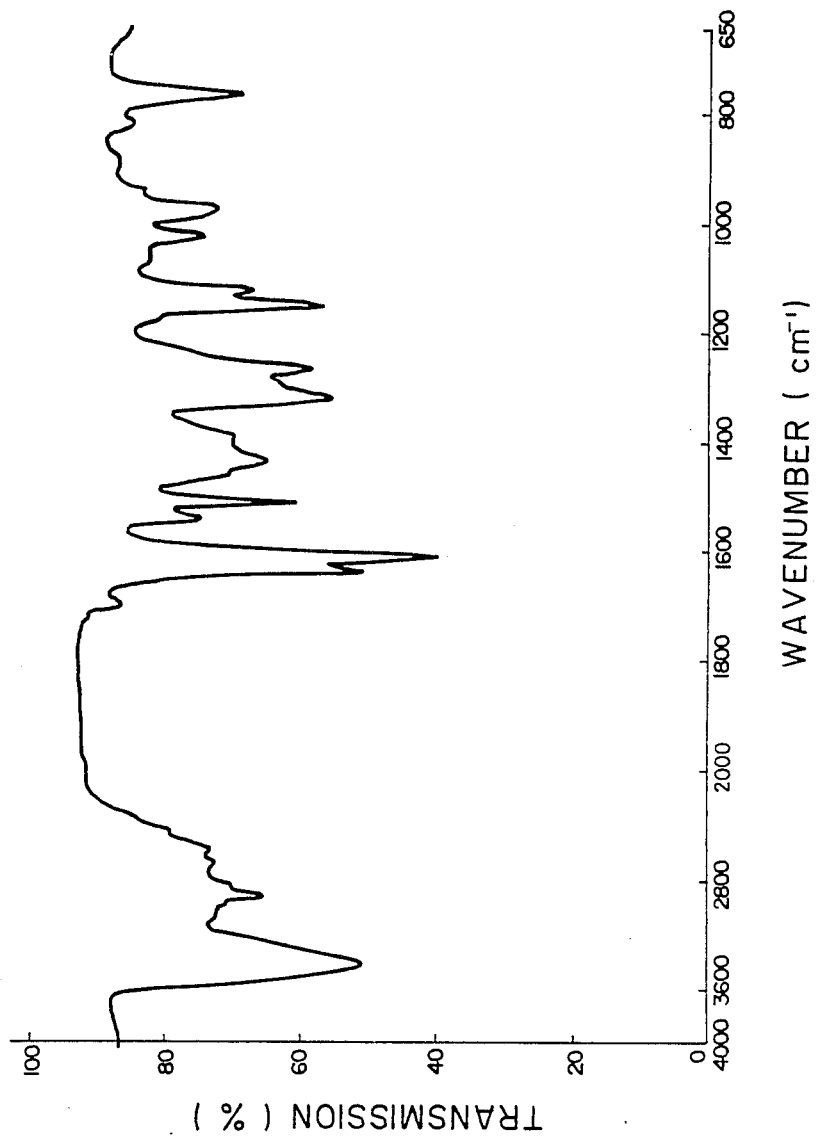

In the similar manner,

5-[4-[4-(2-pyridyl)-1-piperazinyl]-1-hydroxybutyl]-2-methoxy-N-carbamoylaniline (Compound No. 43), 5-[4-[4-(2-pyridyl)-1-piperazinyl]-1-hydroxybutyl]-2-methoxy-N-methanesulfonylaniline dihydrochloride (Compound No. 45), 5-[4-[4-(2-pyridyl)-1-piperazinyl]-1-hydroxybutyl]-2-hydroxyacetanilide (Compound No. 47) and 5-[4-[4-(2-pyridyl)-1-piperazinyl]-1-hydroxybutyl]-2-methylthioacetanilide (Compound No. 48) were prepared, whose characteristics being also shown in Table 1. And, IR spectrum of the compound (Compound No. 45) was shown in FIG. 9 of the accompanying drawings.

TABLE 1

$$R^1\text{-}C_6H_3(R^2)\text{-}Z(CH_2)_n\text{-}N\text{-piperazinyl-}N\text{-}Ar$$

| Compound No. | $R^1$ | $R^2$ | Z | n | Ar | salt | melting (°C.) | elementary analysis C (%) | H (%) | N (%) |
|---|---|---|---|---|---|---|---|---|---|---|
| 1 | —OCH$_3$ | —SO$_2$NH$_2$ | —C=O— | 4 | phenyl | — | 148–150 | calcd. 61.23 found 60.89 | 6.77 6.71 | 9.74 9.59 |
| 2 | " | " | " | " | 2-methoxyphenyl | 2HCl | 165–169 | calcd. 51.68 found 51.35 | 6.22 6.13 | 7.86 7.98 |
| 3 | " | " | " | " | 2-methylphenyl | — | 149–151 | calcd. 62.00 found 62.31 | 7.01 6.98 | 9.43 9.32 |
| 4 | " | " | " | " | 2-chlorophenyl | 2HCl | 145–152 | calcd. 49.03 found 48.78 | 5.61 5.51 | 7.80 7.99 |
| 5 | —SCH$_3$ | " | " | " | phenyl | — | 145–146 | calcd. 57.00 found 57.28 | 6.31 6.37 | 9.06 9.19 |
| 6 | " | " | " | " | 2-methoxyphenyl | — | 176–178 | calcd. 57.84 found 57.43 | 6.54 6.50 | 8.80 8.56 |
| 7 | —S(=O)CH$_3$ | " | " | " | " | — | 184–186 | calcd. 55.96 found 55.66 | 6.33 6.21 | 8.51 8.71 |
| 8 | —SCH$_3$ | " | —CH(OH)— | " | phenyl | — | 83 | calcd. 56.75 found 56.95 | 6.71 6.65 | 9.02 8.86 |

TABLE 1-continued

Structure: R¹, R² on benzene ring with Z(CH₂)ₙ−N(piperazine)−Ar

| Compound No. | R¹ | R² | Z | n | Ar | salt | melting (°C.) | elementary analysis | | |
|---|---|---|---|---|---|---|---|---|---|---|
| | | | | | | | | | C (%) | H (%) | N (%) |
| 9 | —OCH₃ | " | —C=O— | 3 | 2-pyridyl | — | 163–164 | calcd. found | 57.40 57.13 | 6.26 6.34 | 13.39 13.20 |
| 10 | " | " | —CH(OH)— | " | " | 2HCl | 168–170 | calcd. found | 57.12 57.38 | 6.71 6.72 | 13.32 13.42 |
| 11 | —OH | —CONH₂ | —C=O— | 4 | phenyl | — | 219–222 | calcd. found | 69.27 69.59 | 7.13 7.08 | 11.02 11.12 |
| 12 | " | " | " | " | 2-methoxyphenyl | — | 202–205 | calcd. found | 67.13 67.41 | 7.10 7.17 | 10.21 10.38 |
| 13 | " | " | " | " | 2-chlorophenyl | — | 213–218 | calcd. found | 63.53 63.22 | 6.30 6.21 | 10.10 10.21 |
| 14 | " | " | " | " | 2-pyridyl | — | 133–136 | calcd. found | 65.95 66.21 | 6.85 6.92 | 14.65 14.50 |
| 15 | " | —COOH | " | " | " | — | 235–241 | calcd. found | 65.78 65.49 | 6.57 6.62 | 10.96 10.81 |
| 16 | " | " | " | " | 2-methoxyphenyl | — | 225–229 | calcd. found | 67.59 67.94 | 7.09 7.18 | 6.57 6.20 |
| 17 | " | " | —CH(OH)— | " | 2-pyridyl | — | 157–160 | calcd. found | 65.43 65.66 | 7.06 7.00 | 10.90 11.06 |
| 18 | " | —CONH₂ | —C=O— | 3 | " | — | 210–213 | calcd. found | 65.20 65.42 | 6.57 6.49 | 15.21 15.41 |
| 19 | " | —COOCH₃ | " | " | " | — | 190–191 | calcd. found | 65.78 65.50 | 6.57 6.50 | 10.96 10.84 |
| 20 | " | —COOH | " | " | " | — | 248–258 | calcd. found | 65.03 64.78 | 6.28 6.23 | 11.37 11.22 |
| 21 | " | —CONH₂ | —CH(OH)— | " | " | — | 194–196 | calcd. found | 64.85 64.63 | 7.07 7.01 | 15.12 15.28 |

TABLE 1-continued

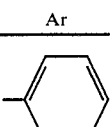

| Compound No. | R¹ | R² | Z | n | Ar | salt | melting (°C.) | elementary analysis | | |
|---|---|---|---|---|---|---|---|---|---|---|
| | | | | | | | | | C (%) | H (%) | N (%) |
| 22 | " | " | " | " | 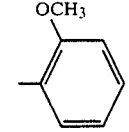 | 2HCl | hygroscopic | calcd. found | 57.02 57.30 | 6.61 6.53 | 9.50 9.68 |
| 23 | " | —NHCOCH₃ | —C=O— | 4 |  OCH₃ | 2HCl | 174–177 | calcd. found | 58.83 59.10 | 6.67 6.48 | 8.43 8.57 |
| 24 | —OCH₃ | " | " | " | " | 2HCl | 155–157 | calcd. found | 58.59 58.36 | 6.88 6.75 | 8.20 8.11 |
| 25 | " | $-\underset{\underset{O}{\|}}{NHCNH_2}$ | " | " | 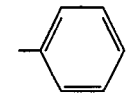 | — | 154–155 | calcd. found | 67.29 67.02 | 7.37 7.26 | 13.65 13.54 |
| 26 | " | " | " | " | 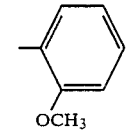 OCH₃ | — | 120–121 | calcd. found | 65.43 65.78 | 7.32 7.37 | 12.72 12.50 |
| 27 | " | " | " | " | 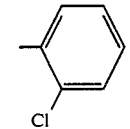 Cl | — | 144–146 | calcd. found | 62.08 62.32 | 6.57 6.63 | 12.59 12.71 |
| 28 | " | " | " | " | 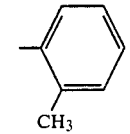 CH₃ | — | 134–135 | calcd. found | 67.90 67.65 | 7.60 7.54 | 13.20 13.29 |
| 29 | " | —NHSO₂CH₃ | " | " | 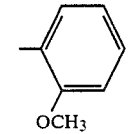 OCH₃ | 2HCl | 149–155 | calcd. found | 52.55 52.30 | 6.43 6.31 | 7.66 7.45 |
| 30 | —SCH₃ | —NHCOCH₃ | " | " | " | — | 80–81 | calcd. found | 65.91 66.18 | 7.30 7.19 | 9.22 9.33 |
| 31 | $\underset{-SCH_3}{\overset{O}{\uparrow}}$ | " | " | " | " | — | 178–180 | calcd. found | 63.67 63.48 | 7.05 6.96 | 8.91 8.80 |
| 32 | $\underset{-SCH_3}{\overset{O_2}{\|}}$ | " | " | " | " | — | 195–197 | calcd. found | 61.58 61.91 | 6.82 6.93 | 8.62 8.79 |
| 33 | —SCH₃ | $-\underset{\underset{O}{\|}}{NHCNH_2}$ | " | " |  | — | 138–139 | calcd. found | 64.76 64.47 | 7.09 7.14 | 13.13 13.01 |

TABLE 1-continued

Structure: R¹, R² on phenyl ring, Z(CH₂)ₙ-N(piperazine)N-Ar

| Compound No. | R¹ | R² | Z | n | Ar | salt | melting (°C.) | elementary analysis C (%) | H (%) | N (%) |
|---|---|---|---|---|---|---|---|---|---|---|
| 34 | " | " | " | " | 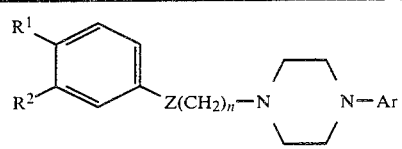 (2-methoxyphenyl) | — | 165–167 | calcd. 63.13 found 63.43 | 7.06 6.98 | 12.27 11.97 |
| 35 | -S(=O)CH₃ | " | " | " | " | — | 168–170 | calcd. 60.99 found 60.79 | 6.82 6.73 | 11.85 11.76 |
| 36 | -OH | " | " | " | " | — | 177–179 | calcd. 64.77 found 65.05 | 7.09 7.01 | 13.14 13.27 |
| 37 |  (3-oxothiomorpholinyl) | | " | " | " | — | 129–131 | calcd. 65.58 found 65.27 | 6.65 6.54 | 9.56 9.67 |
| 38 | 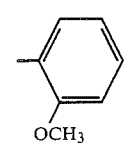 (S-oxide of 37) | | " | " | " | — | 175–178 | calcd. 63.28 found 63.43 | 6.42 6.51 | 9.22 9.33 |
| 39 |  (S,S-dioxide) | | " | " | " | — | 191–193 | calcd. 61.13 found 61.48 | 6.20 6.32 | 8.91 9.03 |
| 40 | 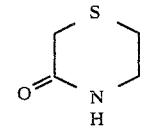 (3-oxomorpholinyl) | | " | " | " | — | 145–146 | calcd. 68.07 found 67.68 | 6.90 6.81 | 9.92 9.80 |
| 41 | 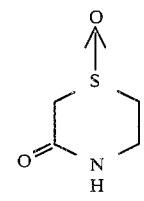 (7-membered oxo-oxazepine) | | " | " | " | — | 72 | calcd. 68.63 found 68.41 | 7.14 7.03 | 9.60 9.76 |
| 42 | -OCH₃ | -NHC(=O)NH₂ | " | 3 | 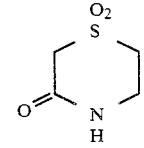 (2-pyridyl) | — | 157–159 | calcd. 63.46 found 63.79 | 6.85 6.64 | 17.62 17.87 |
| 43 | " | " | -CH(OH)- | " | " | — | 83–84 | calcd. 63.14 found 63.45 | 7.32 7.21 | 17.53 17.38 |
| 44 | " | -NHSO₂CH₃ | -C(=O)- | " | " | — | 150–153 | calcd. 58.31 found 58.08 | 6.52 6.44 | 12.95 13.14 |

TABLE 1-continued $$\underset{R^2}{\overset{R^1}{\diagdown}}\!\!\!\!\!\!\!\!\!\!\!\!\!\bigcirc\!\!\!\!-Z(CH_2)_n-N\diagup\!\!\diagdown N-Ar$$

| Compound No. | R¹ | R² | Z | n | Ar | salt | melting (°C.) | elementary analysis | C (%) | H (%) | N (%) |
|---|---|---|---|---|---|---|---|---|---|---|---|
| 45 | " | " | —CH—<br>\|<br>OH | " | " | 2HCl | 140–143 | calcd.<br>found | 49.70<br>49.48 | 6.36<br>6.59 | 11.04<br>11.16 |
| 46 | —OH | —NHCOCH₃ | —C=O— | " | " | — | 76–77 | calcd.<br>found | 65.95<br>66.30 | 6.85<br>6.91 | 14.65<br>14.41 |
| 47 | " | " | —CH—<br>\|<br>OH | " | " | — | 178–179 | calcd.<br>found | 65.60<br>65.79 | 7.34<br>7.30 | 14.57<br>14.31 |
| 48 | —SCH₃ | " | " | " | " | — | 132–133 | calcd.<br>found | 63.74<br>63.98 | 7.29<br>7.13 | 13.51<br>13.37 |
| 49 | 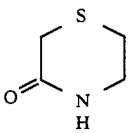 | | —C=O— | " | " | — | 154–155 | calcd.<br>found | 63.61<br>63.31 | 6.10<br>6.05 | 14.13<br>14.01 |
| 50 | " | | —CH—<br>\|<br>OH | " | " | — | 186–188 | calcd.<br>found | 63.29<br>63.42 | 6.58<br>6.60 | 14.06<br>14.19 |
| 51 | —OCH₃ | O<br>\|\|<br>—NHCNH₂ | —C=O— | " | 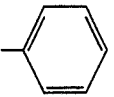 | — | 159–161 | calcd.<br>found | 66.64<br>66.29 | 7.12<br>7.08 | 14.13<br>14.34 |

EXAMPLE 14

Acute toxicity

The present compound was orally administered to mouse and the acute toxicity value (LD₅₀) was calculated according to Litchfield-Wilcoxon method. The results are shown in Table 2.

TABLE 2

| Compound No. | LD₅₀ (mg/kg) |
|---|---|
| 6 | >3000 |
| 12 | >3000 |
| 26 | 2700 |
| 35 | >3000 |

EXAMPLE 15

Hypotensive activity

As the experimental animal, spontaneous hypertensive rats 5 to 7 months after birth with a body weight of 300 to 370 g were used. The blood pressure and the heart beat of the non-narcotized, heart-catheterized rats were operatively determined to calculate the averages in blood pressure and heart beat prior to the administration of the present compound. Successively during 6 hours after orally administering the present compound, the blood pressure and the heart beat were determined to calculate the hypotensive ratio by the following formula:

$$\text{hypotensive ratio (\%)} = \frac{X - Y}{X} \times 100$$

wherein

X is the average in blood pressure before administration; and

Y is the value of the lowest blood pressure after the administration.

The results are shown in Table 3.

TABLE 3

| Compound No. | dose (mg/kg)<br>Hypotensive ratio (%) | | | |
|---|---|---|---|---|
| | 0.3 | 1 | 3 | 10 |
| 2 | 10.5 | 34.6 | 19.7 | — |
| 6 | — | 16.1 | 24.3 | 23.0 |
| 7 | — | 8.9 | 17.5 | 31.3 |
| 12 | — | — | 35.2 | — |
| 13 | — | — | 19.7 | 16.5 |
| 17 | — | — | 21.1 | 15.7 |
| 23 | — | — | 36.5 | — |
| 26 | — | — | 31.8 | — |
| 29 | — | 22.8 | 37.3 | — |
| 34 | — | 17.6 | 28.9 | 39.9 |
| 35 | 16.5 | 16.1 | 25.6 | 47.9 |
| 41 | 25.9 | 33.0 | 35.6 | — |
| 49 | — | 10.9 | 45.7 | — |
| Control 1 | — | 10.5 | — | 2.5 |
| 2 | — | 9.9 | 13.7 | 6.6 |

TABLE 3-continued

| Compound No. | dose (mg/kg) Hypotensive ratio (%) | | | |
|---|---|---|---|---|
| | 0.3 | 1 | 3 | 10 |
| 3 | — | — | 5.6 | 9.4 |

Control 1
5-[2-(4-phenyl-1-piperazinyl)-1-hydroxyethyl]-2-methoxy-benzenesulfonamide
Control 2
5-[2-(4-phenyl-1-piperazinyl)acetyl]salicylamide
Control 3
5-[2-(4-phenyl-1-piperazinyl)-1-hydroxyethyl]-2-methoxy-N—carbamoylaniline

What is claimed is:

1. A piperazine compound of formula (I):

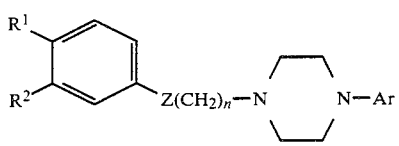

wherein
R[1] is —OH, —OR[3], —SR[3], —SOR[3] or —SO$_2$R[3], wherein R[3] is an alkyl group having 1 to 3 carbon atoms;
R[2] is —SO$_2$NH$_2$, —SO$_2$NHR[4], —SO$_2$NR[4]R[5], —COOH, —COOR[4], —CONH$_2$, —CONHR[4], —CONR[4]R[5], —NHCONH$_2$, —NHCSNH$_2$, —NHCONHR[4], —NHCOR[4] or —NHSO$_2$R[4], wherein R[4] and R[5] are independently alkyl groups having 1 to 3 carbon atoms; or
R[1] and R[2] together with the carbon atoms to which they are attached form

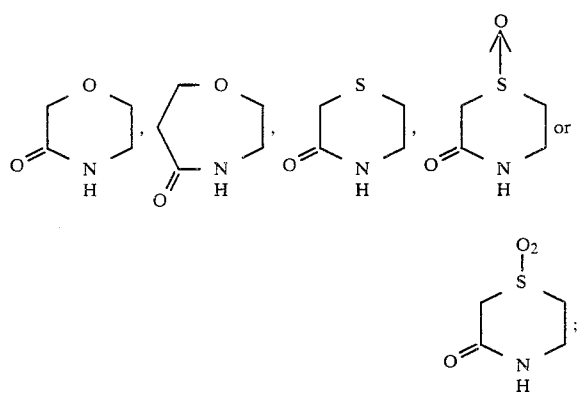

Z is —CO— or —CH(OH)—;
Ar is pyridyl, phenyl, or halogen, C$_{1-3}$ alkyl or C$_{1-3}$ alkoxy substituted phenyl;
n is an integer of 3 to 5; and
therapeutically active acid addition salts thereof.

2. The compound according to claim 1, wherein R$_2$ is —SO$_2$NH$_2$, —SO$_2$NHR[4] or —SO$_2$NR[4]R[5] and the others are as defined in claim 1.

3. The compound according to claim 1, wherein R[1] is —OH or —OR[3], R[2] is —COOH, —COOR[4], —CONH$_2$, —CONHR[4] or —CONR[4]R[5] and the others are as defined in claim 1.

4. The compound according to claim 1, wherein R[2] is —NHCONH$_2$, —NHCSNH$_2$, —NHCONHR[4], —NHCOR[4] or —NHSO$_2$R[4] and the others are as defined in claim 1.

5. The compound according to claim 1, wherein phenyl is substituted with methoxy.

6. The compound according to claim 1, wherein the acid addition salt is dihydrochloride.

7. A pharmaceutical composition which is effective in the treatment of hypertension, comprising:
at least one piperazine compound of the formula (I):

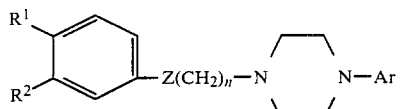

wherein
R[1] is —OH, —OR[3], —SR[3], —SOR[3] or —SO$_2$R[3], wherein R[3] is an alkyl group having 1 to 3 carbon atoms;
R[2] is —SO$_2$NH$_2$, —SO$_2$NHR[4], —SO$_2$NR[4]R[5], —COOH, —COOR[4], —CONH$_2$, —CONHR[4], —CONR[4]R[5], —NHCONH$_2$, —NHCSNH$_2$, —NHCONHR[4], —NHCOR[4] or —NHSO$_2$R[4], wherein R[4] and R[5] are indepedently alkyl groups having 1 to 3 carbon atoms; or
R[1] and R[2] together with the carbon atoms to which they are attached form

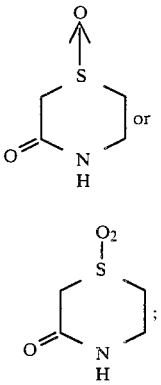

Z is —CO— or —CH(OH)—;
Ar is pyridyl, phenyl, or halogen, C$_{1-3}$ alkyl or C$_{1-3}$ alkoxy substituted phenyl;
n is an integer of 3 to 5; and
therapeutically active acid addition salts thereof in combination with a pharmaceutically acceptable carrier.

8. The composition according to claim 7, wherein said composition is in a solid or liquid dosage unit form intended for oral administration.

9. The composition according to claim 14, wherein said composition is in a liquid dosage unit form intended for parenteral administration.

* * * * *